US012806389B2

(12) United States Patent
Gould

(10) Patent No.: US 12,806,389 B2
(45) Date of Patent: Nov. 24, 2026

(54) DEVICES, SYSTEMS, AND METHODS FOR AUTOMATED DELIVERY OF TOPICAL MEDICATION

(71) Applicant: Daniel J. Gould, Beverly Hills, CA (US)

(72) Inventor: Daniel J. Gould, Beverly Hills, CA (US)

(*) Notice: Subject to any disclaimer, the term of this patent is extended or adjusted under 35 U.S.C. 154(b) by 322 days.

(21) Appl. No.: 18/499,990

(22) Filed: Nov. 1, 2023

(65) Prior Publication Data

US 2025/0135171 A1 May 1, 2025

(51) Int. Cl.
*A61M 35/00* (2006.01)

(52) U.S. Cl.
CPC .................................. *A61M 35/003* (2013.01)

(58) Field of Classification Search
CPC ........ A61M 35/003; A61M 2037/0023; A61M 2037/0061; A61M 37/0015
See application file for complete search history.

(56) References Cited

U.S. PATENT DOCUMENTS 5,593,395 A 1/1997 Martz
11,666,741 B1 * 6/2023 Millikin ................ A61M 37/00 604/500
2005/0228338 A1 * 10/2005 Greenberg .......... A61M 35/003 604/23
2010/0017831 A1 1/2010 Newell
2011/0060274 A1 * 3/2011 Kuhn .................... A61M 5/284 604/82
2016/0114112 A1 * 4/2016 Riebman .......... A61B 17/00491 604/500
2023/0226280 A1 * 7/2023 Lerner ............. A61M 5/31513 604/506

* cited by examiner

*Primary Examiner* — Kai H Weng
(74) *Attorney, Agent, or Firm* — FRESH IP PLC; Michael H. Anderson

(57) ABSTRACT

Disclosed herein are devices, systems, and methods for applying and/or delivering topical compounds (e.g., topical medications) to the surface of mammalian tissue (e.g., skin, mucous membranes, and/or other tissue surfaces). Specifically, disclosed embodiments include a device that is configured to connect to one or more types of known syringes, and, in particular, to one or more types of known syringe tips. At least one embodiment of the device comprises a cap and a membrane, where the cap includes an open connector end for engaging and/or attaching to a syringe via a syringe tip, a delivery end opposite to the connector end, and a cap body disposed between, and connecting, the connector end and the delivery end. The delivery end can further be connected to the membrane by, for instance, inserting one end of the membrane into the delivery end.

22 Claims, 26 Drawing Sheets

DEVICES, SYSTEMS, AND METHODS FOR AUTOMATED DELIVERY OF TOPICAL MEDICATION

FIELD

The disclosure relates generally to devices, systems, and methods for the automated and/or automatic delivery of a topical compound, such as topical medications, to the surface of human tissue (e.g., skin). In particular, embodiments of the disclosure are directed to an automated device that includes one or more syringes and one or more tip portions. The tip portions can be configured to connect to one or more existing types of syringe tips, thereby permitting a user to use the syringe to apply and/or deliver a topical medication for medical (e.g., to treat medical conditions) and/or cosmetic (e.g., to improve skin texture) purposes.

BACKGROUND

Topical compounds are used in a variety of applications and industries to treat the surface of specific tissues, such as skin. For instance, in medicine, topical medications (e.g., processed human derived components, autogenous materials, allograft materials, steroids, anti-scarring medication, growth factors, and exosomes that encourage skin growth) are used to treat various medical conditions, such as, for instance, scarring, burns, and other skin conditions (e.g., hyperpigmentation, inflammation, fibrosis, and the like).

Additionally, topical compounds can be used for cosmetic benefits, such as, for instance, to prevent skin aging and to improve skin texture, quality, and/or clarity.

However, the application of topical compounds requires a device that is capable of both accurately and precisely applying such compounds. For instance, a medical professional or other user must be able to apply an accurate amount of a topical compound (e.g., a topical medication) to a precise area (e.g., a specific section of the skin surface). Such a device should also be easily controllable by the individual applying the compound in order to reduce waste, prevent overmedication, and the like.

Given the foregoing, there exists a significant need for devices, systems, and methods that can apply and/or deliver topical compounds, such as topical medications, to the surface of human tissue (e.g., skin). In particular, there is a need for devices that are compatible with known products (e.g., syringes) to provide improved control of the dispensation (e.g., the method and amount of dispensing) of such topical compounds.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In certain embodiments, the disclosed embodiments may include one or more of the features described herein.

Embodiments of the present disclosure are directed towards devices, systems, and methods for applying and/or delivering one or more topical compounds (e.g., topical medication) to the surface of mammalian tissue (e.g., skin, mucous membranes, and/or other tissue surfaces). At least one embodiment comprises a device that is configured to be engaged with and/or attached to a syringe, and specifically, a syringe tip.

In at least one embodiment, a device for applying and/or delivering one or more topical compounds is disclosed, the device comprising a cap and a membrane. The cap may be hollow and may comprise a first end (alternatively referred to herein as a "connector end") for engaging with and/or attaching to a syringe (e.g., any known syringe) via the syringe tip, a second end (alternatively referred to herein as a "delivery end") disposed opposite to the connector end, and a cap body disposed between, and connecting, the connector end and the delivery end. Additionally, the connector end and the delivery end may be fluidly connected. The aforementioned membrane may be connected, either detachably or fixably, to the delivery end.

In at least a further embodiment, the connector end comprises one or more connection mechanisms known for syringe tips, including, for instance, a luer-style connector, a slip-on connection, a push-on connection, an eccentric tip, a tapered tip, a catheter tip, and combinations thereof. The device may therefore, in at least one embodiment, be engaged with and/or attached to a tip for any known type of syringe, including, for instance, a disposable syringe, a safety syringe, an insulin syringe, a hypodermic syringe, a multi-shot needle syringe, a venom extraction syringe, an oral syringe, a dental syringe, a dose-sparing syringe, a glass syringe, a plastic syringe (e.g., a polyethylene syringe), and combinations thereof.

In at least an additional embodiment, a device for delivering one or more topical compounds to a surface of human tissue is disclosed. The device comprises a syringe, a cap, and a membrane. The syringe comprises a barrel and a syringe tip fluidly connected to the barrel. The cap comprises an open connector end, an open delivery end fluidly connected to the open connector end, and a cap body disposed between, and connecting, the open connector end and the open delivery end. The membrane comprises a delivery surface and is connected to the open delivery end such that the delivery surface closes the open delivery end.

In at least a further embodiment, the open connector end is releasably connected to the syringe tip such that one or more openings in the syringe tip are fluidly connected to the cap. Such releasable connection may be provided by a connector and/or connection mechanism such as, for instance, a luer-style connector, a slip-on connection, a push-on connection, an eccentric tip, a tapered tip, a catheter tip, and combinations thereof.

Thus, a user may use the device by, for instance, exerting force on a portion of the syringe (e.g., the barrel of the syringe) to move one or more topical compounds from the barrel of the syringe through the syringe tip and through the device, thereby extruding at least a portion of the one or more topical compounds through the attached membrane. Such portion may then be applied to the surface of human tissue. It should therefore be appreciated that, in at least one embodiment, the membrane is selectively permeable such that the membrane permits the one or more compounds inside the syringe to move through the membrane. Non-limiting examples of membrane materials include, for instance, one or more polymers (including synthetic/man-made polymers), one or more resins, etc. Thus, the membrane may be composed of, for instance, cellulose, gauze, and the like.

The one or more compounds may be one or more topical medications or other compounds, in any formulation or concentration, including, for instance, triamcinolone, fluorouracil (also known as "5-FU"), tranexamic acid (also known as "TXA"), azelaic acid, one or more bleaching agents (e.g., hydroquinone), one or more topical numbing agents (e.g., lidocaine, bupivacaine), one or more topical antibiotics, one or more dyes or stains (e.g., bonnet blue, gentian violet), one or more topical anti-inflammatory compounds such as nonsteroidal anti-inflammatory drugs (e.g., diclofenac, ibuprofen, Toradol), vitamins (e.g., vitamin A, vitamin B12, vitamin E, vitamin K), one or more topical steroids, one or more topical darkening agents for conditions such as hypopigmented scars (e.g., bimatoprost), anti-oxidants (e.g., N-acetyl-cysteine, glutathione), one or more micro-dosed compounds (e.g., botulinum toxin, hyaluronic acid, other compounds used in micro-needling reservoir treatments), one or more skincare compounds, one or more cosmetic compounds, one or more nutraceutical compounds, and combinations thereof.

Such compounds can be used to treat a variety of conditions, including, for instance, skin conditions such as scars, burns, hyperpigmentation, inflammation, and/or fibrosis. Purely as non-limiting examples, the device could be used to deliver (1) topical steroids to treat scars, (2) growth factors and anti-scarring medications to treat burns, (3) anti-aging compounds and/or vitamins to improve skin texture, quality, and/or clarity, (4) anti-inflammatory compounds to prevent and/or treat inflammation, and (5) medication or other treatment compounds as part of skin laser treatments, microneedling, dermal abrasion, and the like.

In at least an additional embodiment, a method is disclosed herein for delivering one or more topical compounds to a surface of human tissue. The method comprises obtaining an applicator having one or more topical compounds to be delivered, wherein the applicator comprises a cap and a membrane, wherein the cap comprises one end connected to the membrane, wherein the cap comprises an inner area; exerting force on the applicator to move the one or more topical compounds through the inner area and through the one end, such that at least one portion of the one or more topical compounds are extruded through the membrane; and positioning the applicator adjacent to a surface of human tissue such that the at least one portion of the one or more topical compounds contacts the surface, thereby delivering the one or more topical compounds.

In at least a further embodiment, the applicator comprises a syringe, which may be any syringe described herein and/or any known syringe. The syringe may comprise a barrel fluidly connected to a syringe tip, which may be any syringe tip described herein and/or any known syringe tip. The cap may further comprise a connector end that is configured to attach, either releasably or non-releasably, to the syringe tip, such that one or more openings in the syringe tip are fluidly connected to the connector end. Further, the cap may comprise a delivery end disposed opposite the connector end, wherein the delivery end is fluidly connected to the connector end.

In at least one embodiment, the method may further comprise engaging the membrane with the one end of the cap, and/or engaging the connector end of the cap with a syringe tip of a syringe.

In at least an additional embodiment, the aforementioned exerting force on the applicator may further comprise engaging the membrane with the one end of the cap, and/or engaging the connector end of the cap with a syringe tip of a syringe. The aforementioned exerting force on the applicator may additionally comprise (1) exerting the force on the barrel of the syringe, thereby moving the one or more topical compounds through the syringe tip and through the connector end, and/or (2) holding the applicator between a thumb and at least one finger of one hand.

Thus, a user of the method may, in at least one embodiment, hold the applicator in such a fashion to provide one or more benefits when compared with known methods of holding a syringe, in which the user's thumb contacts a top surface of the plunger of the syringe, rather than the syringe barrel, in order to exert force on the plunger to depress the plunger into the barrel, thereby ejecting the one or more compounds inside the barrel through a needle attached to the syringe tip.

Such aforementioned one or more benefits may include, for instance, more and/or better control of the amount of the one or more compounds applied, limiting the amount of the one or more compounds applied, more and/or better control of the surface area to which the one or more compounds are applied, prevention of overmedication, prevention of waste, and/or cost savings from avoiding excessive application amounts of the one or more compounds.

In at least one embodiment, an automated device for applying and/or delivering topical compounds is disclosed, the automated device having one or more areas and/or portions that are physically manipulatable to trigger one or more automated aspects. These areas and/or portions can be of any physically manipulatable construction (e.g., a tab, a lever, a button, etc.).

In at least an additional embodiment, the automated device comprises a portion that can be physically manipulated to automatically move a plunger and/or ejector. The portion may, in at least one example, be located on a tip of the plunger. The portion may, in at least another example, be located on a surface (e.g., a side surface) of the syringe.

In at least an additional embodiment, the automated device comprises a plunger and/or ejector that operates under electric power (e.g., via one or more batteries disposed within the device, via a charger and/or charging mechanism that can be plugged into an electric socket, etc.).

In at least an additional embodiment, the automated device comprises an automated connector between a syringe portion and a tip portion. In at least one example, the automated connector can automatically attach the syringe portion with the tip portion. In at least another example, the automated connector can automatically detach the syringe portion from the tip portion. Such automatic attachment and/or detachment may be achieved via physical manipulation of a tab, button, and/or lever disposed anywhere on the device.

In at least an additional embodiment, the automated device comprises a capsule containing one or more topical compounds, the capsule releasing the one or more topical compounds upon physical contact with the capsule and/or puncture of the capsule. The release of the one or more topical compounds can occur automatically (e.g., physical manipulation of a tab, button, and/or lever) and/or via contact with a plunger and/or ejector, which itself may be moveable automatically.

In at least an additional embodiment, the automated device comprises an area that can be physically manipulated (e.g., moved, pressed, depressed, etc.) to trigger automatic loading of one or more portions of the topical compounds from a syringe portion into a tip portion. In at least one example, such loading occurs without the one or more portions being released out of the tip portion.

In at least an additional embodiment, the automated device comprises an area that can be physically manipulated (e.g., moved, pressed, depressed, etc.) to trigger automatic aspiration of a fluid and/or liquid into the automated device or any portion thereof (e.g., a syringe portion of the device).

In at least an additional embodiment, the automated device comprises an area that can be physically manipulated (e.g., moved, pressed, depressed, etc.) to trigger automatic removal of any air inside the device (e.g., before filling the device with one or more topical compounds). Such automatic removal may, in at least one example, be achieved by a plunger and/or ejector.

In at least an additional embodiment, the automated device comprises automated sensors that detect a distance and/or proximity of the device or one or more portions thereof to a surface of human tissue (e.g., skin).

In at least an additional embodiment, the automated device comprises an automated alarm or other notification (e.g., an audio alarm, a visual light, and the like) to notify a user to prevent improper use and/or misuse of the device.

In at least an additional embodiment, the automated device comprises a filter to filter one or more topical compounds before delivery and/or administration. In at least one example, filtration through the filter occurs when an area is physically manipulated (e.g., moved, pressed, depressed, etc.) by a user.

In at least an additional embodiment, the automated device comprises one or more locking mechanisms that automatically move and/or automatically lock or otherwise disable one or more portions of the device. In at least one example, the one or more locking mechanisms automatically move and/or automatically lock a plunger and/or ejector once the plunger has been fully depressed and/or all of the topical compounds in the device have been delivered, administered, and/or ejected.

In at least an additional embodiment, the automated device further comprises a storage area that can be automatically activated to release one or more additional agents into the barrel or chamber. In at least one example, such release is achieved when an area is physically manipulated (e.g., moved, pressed, depressed, etc.) by a user.

In at least an additional embodiment, the automated device further comprises a cover that can be moved and/or locked in place to cover one or more portions of the device. In at least one example, the cover is moveable on one or more arms. Movement and/or locking of the cover is achieved when an area is physically manipulated (e.g., moved, pressed, depressed, etc.) by a user.

These and further and other objects and features of the invention are apparent in the disclosure, which includes the above and ongoing written specification, as well as the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

DETAILED DESCRIPTION

Figure 1A:
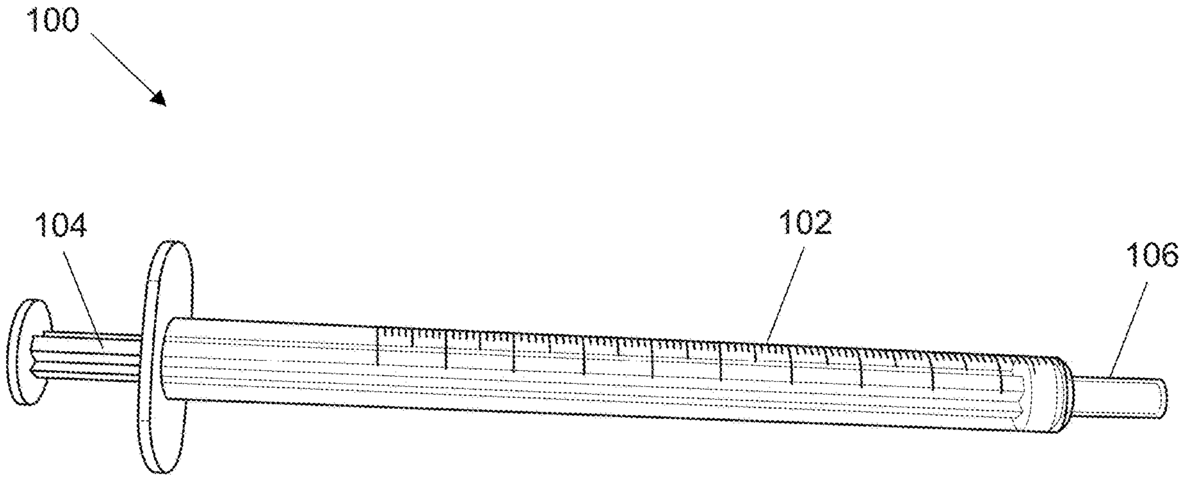
FIGS. 1A-1C show non-limiting examples of syringes, including a syringe with a luer-style connector (FIG. 1C).

The present invention is more fully described below with reference to the accompanying figures. The following description is exemplary in that several embodiments are described (e.g., by use of the terms "preferably," "for example," or "in one embodiment"); however, such should not be viewed as limiting or as setting forth the only embodiments of the present invention, as the invention encompasses other embodiments not specifically recited in this description, including alternatives, modifications, and equivalents within the spirit and scope of the invention. Further, the use of the terms "invention," "present invention," "embodiment," and similar terms throughout the description are used broadly and not intended to mean that the invention requires, or is limited to, any particular aspect being described or that such description is the only manner in which the invention may be made or used. Additionally, the invention may be described in the context of specific applications; however, the invention may be used in a variety of applications not specifically described.

The embodiment(s) described, and references in the specification to "one embodiment," "an embodiment," "an example embodiment," etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted. Further, the description is not to be taken in a limiting sense, but is made merely for the purpose of illustrating the general principles of the invention, since the scope of the invention is best defined by the appended claims.

It will be understood that, although the terms "first," "second," etc. may be used herein to describe various elements, these elements should not be limited by these terms. These terms are only used to distinguish one element from another. Purely as a non-limiting example, a first element could be termed a second element, and, similarly, a second element could be termed a first element, without departing from the scope of example embodiments. As used herein, the term "and/or" includes any and all combinations of one or more of the associated listed items. As used herein, "at least one of A, B, and C" indicates A or B or C or any combination thereof. As used herein, the singular forms "a," "an," and "the" are intended to include the plural forms as well, unless the context clearly indicates otherwise. It should also be noted that, in some alternative implementations, the functions and/or acts noted may occur out of the order as represented in at least one of the several figures. Purely as a non-limiting example, two figures shown in succession may in fact be executed substantially concurrently or may sometimes be executed in the reverse order, depending upon the functionality and/or acts described or depicted.

Any ranges used herein are in shorthand, so as to avoid having to list and describe each and every value within the range. Any appropriate value within the range can be selected, where appropriate, as the upper value, lower value, or the terminus of the range.

Unless indicated to the contrary, numerical parameters set forth herein are approximations that can vary depending upon the desired properties sought to be obtained. At the very least, and not as an attempt to limit the application of the doctrine of equivalents to the scope of any claims, each numerical parameter should be construed in light of the number of significant digits and ordinary rounding approaches.

The words "comprise," "comprises," and "comprising" are to be interpreted inclusively rather than exclusively. Likewise the terms "include," "including," and "or" should all be construed to be inclusive, unless such a construction is clearly prohibited from the context. The terms "comprising" or "including" are intended to include embodiments encompassed by the terms "consisting essentially of" and "consisting of." Similarly, the term "consisting essentially of" is intended to include embodiments encompassed by the term "consisting of." Although having distinct meanings, the terms "comprising," "having," "containing," and "consisting of" may be replaced with one another throughout the description of the invention.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Terms such as, among others, "about," "approximately," "approaching," or "substantially," mean within an acceptable error for a particular value or numeric indication as determined by one of ordinary skill in the art, which depends in part on how the value is measured or determined. The aforementioned terms, when used with reference to a particular non-zero value or numeric indication, are intended to mean plus or minus 10% of that referenced numeric indication. As an example, the term "about 4" would include a range of 3.6 to 4.4. All numbers expressing dimensions, velocity, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims, each numerical parameter should be construed in light of the number of significant digits and ordinary rounding approaches.

"Typically" or "optionally" means that the subsequently described event or circumstance may or may not occur, and that the description includes instances where said event or circumstance occurs and instances where it does not.

Wherever the phrase "for example," "such as," "including," and the like are used herein, the phrase "and without limitation" is understood to follow unless explicitly stated otherwise.

The term "administering" or "administration" refers to providing or giving a subject one or more agents, compounds, and/or formulations, either alone or in conjunction with any other compound and/or agent (including, e.g., prophylactic or therapeutic agents), by any effective route. Exemplary routes of administration include, but are not limited to, topical administration, as defined further below.

The term "automatic" or "automated" refers to the ability to be used and/or operated in an assisted fashion, with at least some portion of non-human control. The assistance can be partial or complete; that is, the term "automatic" or "automated" can refer to the ability to be used with little or no direct human control.

The terms "agent" or "active agent," which are used interchangeably herein, refer to a physiologically or pharmacologically active substance that acts locally and/or systemically in a subject's body. An "agent" or "active agent" is a compound or substance that is administered to an individual for the treatment (e.g., therapeutic agent, cancer therapeutic agent, and the like), prevention (e.g., prophylactic agent), or diagnosis (e.g., diagnostic agent) of a disease or disorder. Such agents may also include therapeutics that prevent or alleviate symptoms of a disease or disorder.

The term "compound" refers to a substance formed from one or more chemical elements, arranged together in any proportion or structural arrangement. The one or more chemical elements may be either naturally occurring and/or non-naturally occurring. As used herein, the term "biological compound" refers to a compound of biological origin and/or having one or more effects on a subject's local and/or systemic biological functions. Accordingly, "compounds" or "biological compounds" include, as non-limiting examples, various proteins (e.g., growth factors, hormones, enzymes), nucleic acids, and pharmaceutical products (e.g., drugs, prodrugs). The term "drug" generally refers to a medicine or other substance that has a physiological effect when introduced into a subject. The term "prodrug" generally refers to a biologically and/or chemically inactive compound that can be metabolized by a subject to produce a drug.

The term "connector," at least as used herein, refers to an article of manufacture for connecting two or more other articles together. Thus, certain portions of a syringe, such as a syringe tip and a needle, may be connected using one or more different types of connectors. Common connectors used in syringes include a "luer-style connector," a term which, as used herein, encompasses both a lock fitting, in which a tabbed hub on the needle screws into threads on the syringe tip, and a slip fitting, in which the needle and the syringe tip are pressed together, relying on friction (as opposed to screw threads) to hold them together. Other common connectors used in syringes include a slip-on connection, a push-on connection, an eccentric tip, a tapered tip, a catheter tip, and combinations thereof.

The terms "effective amount" or "therapeutically effective amount," which are used interchangeably herein, refer to the amount of an agent that is sufficient to effect beneficial or desired therapeutic result, including clinical results. An "effective amount" may vary depending upon one or more of: the subject and disease condition being treated, the sex, weight and age of the subject, the severity of the disease condition, the manner of administration, the ability of one or more formulations to elicit a desired response in the subject, and the like. The beneficial therapeutic effect can include, but is not limited to, enablement of diagnostic determinations; prevention of a disease; amelioration of a disease, symptom, disorder, and/or pathological condition; reducing or preventing the onset of a disease, symptom, disorder, and/or pathological condition; and generally counteracting a disease, symptom, disorder, and/or pathological condition. The term "effective amount" includes an amount that is effective to "treat" a subject (e.g., a patient or individual). When a therapeutic amount is indicated, the precise amount of one or more formulations to be administered can be determined by a physician, based on, for instance, considerations such as individual differences in age, weight, one or more symptoms, extent of infection or disease progression, and/or condition of the subject (individual).

The term "membrane" refers to a thin sheet that acts as a boundary, barrier, lining, and/or partition. Membranes may exist naturally inside an organism (e.g., a mammal) or be synthetic/manmade. Thus, the thin sheet may be made of, for instance, tissue or one or more layers of cells. Alternatively, the thin sheet may be made of a manmade material (e.g., one or more resins, one or more polymers such as cellulose and thermoplastics, gauze, and the like). Membranes can further be selectively permeable such that only certain molecules and/or types of molecules may cross the membrane from one side to the other.

The term "molecular weight" generally refers to the relative average chain length of a bulk polymer or protein, unless otherwise specified. In practice, molecular weights can be estimated or characterized using various methods including, for example, gel permeation chromatography (GPC) or capillary viscometry. GPC molecular weights are reported as the weight-average molecular weight (MW), as opposed to the number-average molecular weight (MN). Capillary viscometry provides estimates of molecular weight as the inherent viscosity determined from a dilute polymer solution using a particular set of concentration, temperature, and solvent conditions.

The term "peptide" refers to a polymer of amino acid residues. The amino acid residues may be naturally occurring and/or non-naturally occurring. The terms "polypeptide," "peptide," and "protein" are used interchangeably herein. The terms apply to, for instance, amino acid polymers of one or more amino acid residues, an artificial chemical mimetic of a corresponding naturally occurring amino acid, naturally occurring amino acid polymers, and non-naturally occurring amino acid polymers.

The terms "subject," "individual," or "patient," which are used interchangeably herein, refer to a vertebrate, such as a mammal (e.g., a human). Mammals include, but are not limited to, murines (e.g., mice), simians, humans, farm animals, sport animals, and pets. In at least one embodiment, the subject is a non-human mammal, such as a monkey or other non-human primate, mouse, rat, rabbit, guinea pig, pig, goat, sheep, dog, cat, horse, or cow. In at least one example, the subject has a disease or condition that can be treated using one or more agents, formulations, and/or methods (e.g., including the delivery device and/or delivery tip) disclosed herein. In at least an additional example, the subject is a laboratory animal/organism, such as, for example, a mouse, rabbit, guinea pig, or rat. In at least a further example, a subject includes, for instance, farm animals, domestic animals and/or pets (e.g., cats, dogs). In at least a still further example, a subject is a human patient that has a disease or condition, has been diagnosed with a disease or condition, and/or is at risk of having a disease or condition. A "patient" can specifically refer to a subject that has been diagnosed with a particular disease, condition, and/or indication that can be treated with one or more agents, formulations, and/or methods (e.g., including the delivery device and/or delivery tip) disclosed herein.

The term "syringe" refers to a device for intaking and/or expelling one or more agents, compounds, and/or formulations. Generally, a syringe includes the following components: a barrel for holding one or more agents, compounds, and/or formulations to be injected or expelled from the syringe, a plunger that fits inside the barrel and can be pushed or pulled along an inside surface of the barrel, a syringe tip fluidly connected to the barrel and disposed at a front end of the barrel, and a needle that can be attached to the syringe tip or detached from the syringe tip as needed. Certain components of the syringe, including, for instance, the syringe tip and the needle, are connectable and/or connected using a connector, as defined above herein. Common types of syringes include disposable syringes, safety syringes, insulin syringes, hypodermic syringes, multi-shot needle syringes, venom extraction syringes, oral syringes, dental syringes, dose-sparing syringes, glass syringes, plastic syringes (e.g., polyethylene syringes), and combinations thereof.

The term "topical administration" refers to a type of non-invasive administration to one or more tissues (e.g., the skin, orifices, one or more mucosal membranes, and or other tissues) of a subject. Topical administrations can be administered locally; that is, they are capable of providing a local effect in the region of application without systemic exposure. Thus, as a non-limiting example, a topical administration may include application of one or more compounds to a tissue surface. Topical formulations can, additionally, provide one or more systemic effects via, e.g., adsorption into the blood stream of the individual. Routes of topical administration include, but are not limited to, cutaneous and transdermal administration, buccal administration, intranasal administration, inhalation, intravaginal administration, intravesical administration, ophthalmic administration, pulmonary administration, and rectal administration. Accordingly, the term "topical" describes an agent, compound, and/or formulation that may be applied via topical administration.

Further, unless otherwise noted, technical terms are generally used according to conventional usage. Aspects of the disclosure employ, unless indicated specifically to the contrary, conventional methods of chemistry, biochemistry, organic chemistry, molecular biology, microbiology, recombinant DNA techniques, genetics, immunology, and/or cell biology, many of which are described below solely for the purpose of illustration. Such techniques are explained fully in technical literature sources. General definitions of common terms in the aforementioned fields, including, for instance, molecular biology, may be found in references such as, e.g., Krebs et al., *Lewin's Genes X*, Jones & Bartlett Learning (2009) (ISBN 0763766321); Rédei, *Encyclopedic Dictionary of Genetics, Genomics, Proteomics and Informatics* (3rd ed.), Springer (2008) (ISBN: 1402067532); Ausubel et al., *Current Protocols in Molecular Biology*, John Wiley and Sons (updated July 2008) (ISBN: 047150338X); Ausubel et al., *Short Protocols in Molecular Biology: A Compendium of Methods from Current Protocols in Molecular Biology* (2nd ed.), Wiley-Interscience (1989) (ISBN 0471514705); Glover, et al., *DNA Cloning: A Practical Approach, Vol. I-II*, Oxford University Press (1985) (ISBN 0199634777); Anand et al., *Techniques for the Analysis of Complex Genomes*, Academic Press (1992) (ISBN 0120576201); Hames et al., *Transcription and Translation: A Practical Approach*, Oxford University Press (1984) (ISBN 0904147525); Perbal et al., *A Practical Guide to Molecular Cloning* (2nd ed.), Wiley-Interscience (1988) (ISBN 0471850713); Kendrew et al., *Encyclopedia of Molecular Biology*, Wiley-Blackwall (1994) (ISBN 0632021829); Meyers et al., *Molecular Biology and Biotechnology: A Comprehensive Desk Reference*, Wiley-VCH (1996) (ISBN 047118571X); Harlow et al., *Antibodies: A Laboratory Manual*, Cold Spring Harbor Laboratory Press (1988) (ISBN 0879693746); Coligan et al., *Current Protocols in Immunology*, Current Protocols (2002) (ISBN 0471522767); *Annual Review of Immunology*; articles and/or monographs in scientific journals (e.g., *Advances in Immunology*); and other similar references.

Embodiments of the disclosure comprise devices, methods, and/or systems that permit a user to apply and/or deliver topical compounds (e.g., topical medications) to the surface of mammalian tissue (e.g., skin, mucous membranes, and/or other tissue surfaces). At least some such embodiments comprise a device that is connectable to one or more types of known syringes.

A skilled artisan will appreciate that known syringes generally include the following components: a barrel for holding one or more compounds to be injected or expelled from the syringe, a plunger that fits inside the barrel and can be pushed or pulled along an inside surface of the barrel, a syringe tip fluidly connected to the barrel and disposed at a front end of the barrel, and a needle that can be attached to the syringe tip or detached from the syringe tip as needed.

It will further be appreciated that known syringe tips have different kinds of connectors and/or connection mechanisms to connect the syringe tip with the needle. Generally, such connectors are small-scale and/or small bore fittings (e.g., where the size of the connector opening is less than about 8.5 millimeters) for making leak-free connections. One non-limiting example of such a connector and/or connection mechanism is a "luer-style connector," a term which, as used herein, encompasses both a lock fitting, in which a tabbed hub on the needle screws into threads on the syringe tip, and a slip fitting, in which the needle and the syringe tip are pressed together, relying on friction (as opposed to screw threads) to hold them together. Further, the term "luer-style connector" as used herein is not limited to any specific dimensions, name brands, or manufacturers.

Figure 1B:
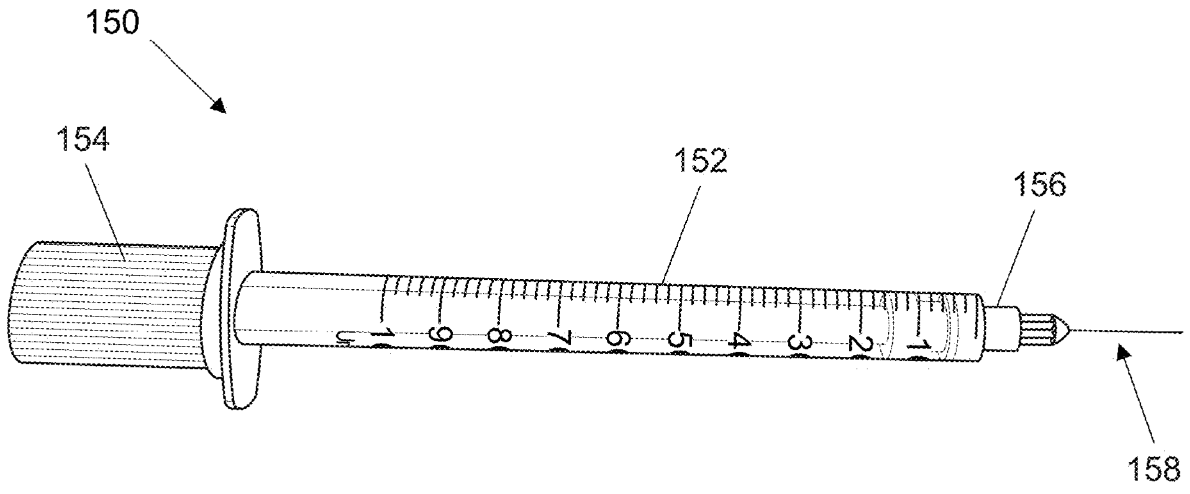

Turning now to FIGS. 1A and 1B, two non-limiting examples of known syringes are shown. FIG. 1A shows a syringe 100 that has a barrel 102, a plunger 104, and a syringe tip 106. The needle is not shown. FIG. 1B shows a syringe 150 that has a barrel 152, a plunger 154, a syringe tip 156, and a needle 158 connected to the syringe tip.

Figure 1C:
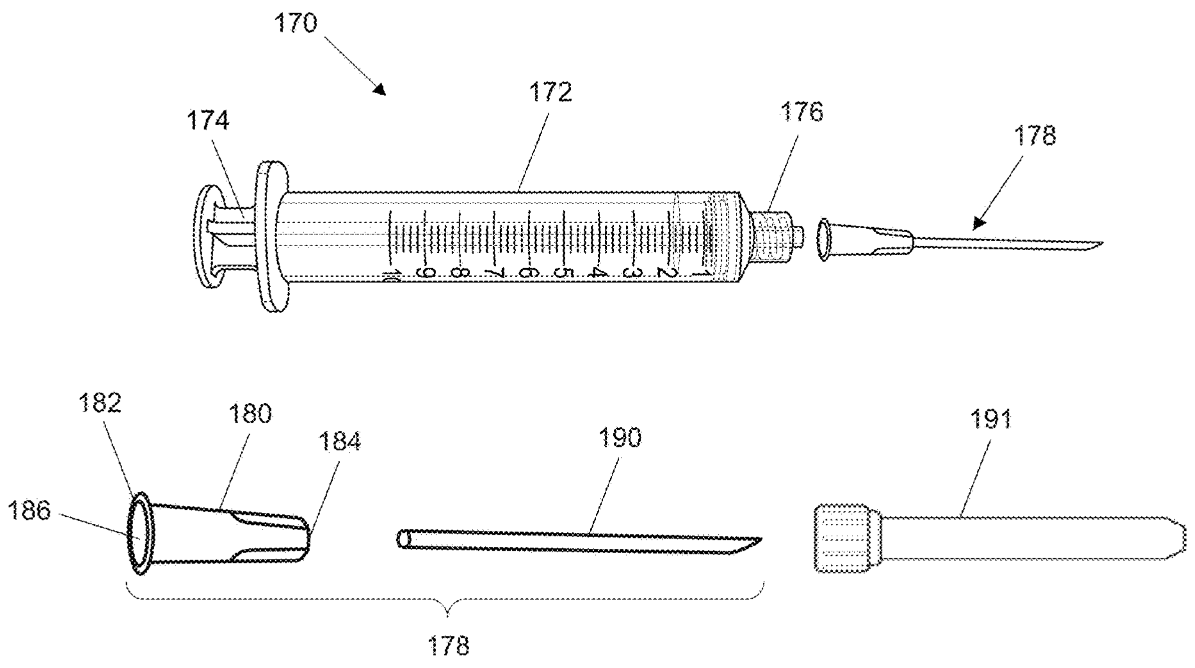
Figure 2A:
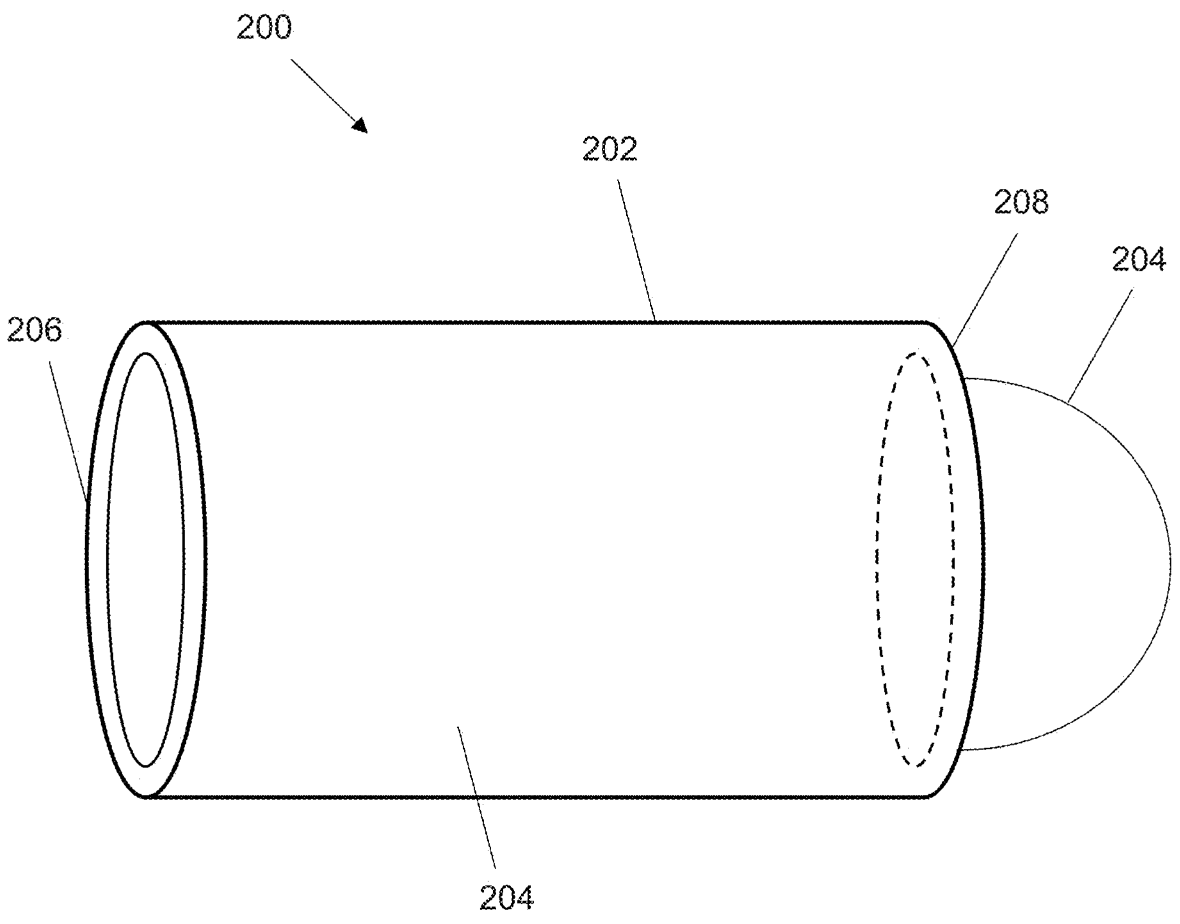
FIGS. 2A-2B show a device for applying topical compounds from both a perspective view (FIG. 2A) and an end view (FIG. 2B), according to at least one embodiment of the present disclosure.

FIG. 1C shows another non-limiting example of a syringe with a luer-style connector. Specifically, a syringe 170 has a barrel 172, a plunger 174, and a syringe tip 176. The syringe tip 176 utilizes a luer-style connector, as described above herein. The needle 178 is shown in a position detached from, and unconnected to, the syringe tip 176. Thus, in at least one embodiment, a device for applying and/or delivering topical compounds (e.g., as shown in FIGS. 2A and/or 2B) may be attached to the syringe tip 176 in lieu of the needle 178.

Also shown in FIG. 1C is an exploded view of the needle 178. The needle 178 includes a hub 180 and a needle tip 190, in addition to an optional cover 191 for covering and/or capping the needle tip. It should be appreciated that other needles disclosed herein (e.g., needle 158) also include a hub, a needle tip, and/or a cover. Accordingly, the description of the needle 178 presented herein is not limited solely to that shown in FIG. 1C. Generally, a "hub" or "needle hub," terms which are used interchangeably herein, is a hollow structure that is configured to engage on one end with a syringe and on another end with the needle tip. Accordingly, the hub 180 is hollow with an inner area 186 that includes a flange 182 that is configured to engage with, and/or attach to, the syringe 170 and, in particular, the syringe tip 176. During use, one or more compounds in the barrel 172 move through the syringe tip 176 and into the inner area 186, before being ejected through the needle tip 190. The needle tip is connectable with, and/or connected to, the hub 180 at a needle tip end 184. Such needle tip end is disposed at one end of the hub 180, e.g., an end distal to the syringe, while the flange 182 is disposed at an opposite end of the hub, e.g., an end proximal to the syringe. The flange 182 is configured to attach the hub 180 and/or the needle tip 190 to the syringe 170 via the syringe tip 176. The flange 182 may be a generally circular structure that engages with, and/or attaches to, the syringe tip 176 via one or more connectors and/or connection mechanisms (e.g., a luer-style connector). Thus, for instance, a lock fitting luer-style connector may be used in which the flange 182 contains one or more tabs that screw into one or more threads on the syringe tip 176. Additional connectors and/or connection mechanisms, as described above herein, may also be used, such as, for instance, a slip-on connection, a push-on connection, an eccentric tip, a tapered tip, a catheter tip, and combinations thereof.

Further variations on the structure of the hub 180 are possible. For instance, in at least one embodiment, one or more extendable sections, fins, and/or grips may be disposed on an outer surface of the hub to assist the user in gripping the hub. In at least another embodiment, the needle tip end 184 may contain one or more structures (e.g., dimples, protrusions, and/or indentations) to assist in engagement and/or connection of the hub 180 with the needle tip 190. In at least a further embodiment, the flange 182 contains one or more marks to assist a user in identifying one or more properties of the syringe and/or needle being used (e.g., syringe type, syringe brand, needle type, needle brand, needle gauge, syringe measurements, including barrel volume measurements, etc.). Non-limiting examples of such marks include color-coding, text, logos, indentations, protrusions, ridges, and the like. In any one or more of the embodiments mentioned herein, the hub 180, and/or one or more portions thereof, may be composed of one or more different materials, including, for instance, one or more plastic polymers (e.g., polypropylene, polyethylene, polycarbonate, thermoplastic elastomers, terephthalate, etc.), one or more resins (e.g., polyactide, starch-filled polypropylene, polyhydroxyalkanoates, etc.), and the like.

The cover 191 is used for covering the needle tip 190. To ensure that the cover does not fall off, one or more connectors and/or connection mechanisms can be used, including any of those described herein. For instance, in at least one embodiment, the cover includes one or more snap-on connections. In at least another embodiment, the cover includes one or more slip-on connections. The cover 191 can perform one or more functions related to the syringe 170, the hub 180, and/or the needle 190, and/or any uses thereof. Such one or more functions include, for instance, preventing the needle tip from being bent or damaged, preventing the needle tip from being partially or completely clogged, preventing the needle tip from injuring or harming (e.g., pricking) a user and/or any other individual (e.g., a patient or subject), preventing one or more compounds and/or formulations in the syringe (e.g., in the barrel) from escaping or leaking out, shielding one or more portions of the syringe (e.g., the needle) from one or more environmental effects (e.g., oxidative effects, corrosive effects, bleaching effects, etc.), shielding one or more portions of the syringe (e.g., the needle) from one or more light wavelengths (e.g., wavelengths below 500 nanometers (nm), wavelengths between 300-500 nm, wavelengths between 290-500 nm, wavelengths between 290-450 nm, wavelengths above 500 nm, wavelengths from 500-800 nm, etc.), and the like. Protection from one or more light wavelengths may be especially important when using the syringe to apply one or more light-sensitive compounds such as, for example, aminophylline, chlorpheniramine maleate, chlorpromazine hydrochloride (HCl), cisplatin, dacarbazine, diazepam, diazoxide, digoxin, diphenhydramine, dopamine HCl, doxycycline hyclate, droperidol, epinephrine HCl, fluorouracil, folic acid, furosemide, haloperidol, hydrocortisone, isoproterenol, levarterenol bitartrate, menadiol sodium diphosphate, methadone, morphine, nitroglycerin, nitroprusside solution, phenylephrine HCl, phytonadione, promethazine, propranolol HCl, streptomycin, testosterone, triflupromazine HCl, vinblastine, vincristine, one or more vitamins (e.g., vitamin B), and the like. The cover 191 may also perform one or more functions related to applying the one or more compounds and/or formulations in the syringe. As a non-limiting example, the cover 191 may store and/or apply one or more secondary compounds that are applied to a subject and/or patient in addition to the one or more compounds and/or formulations in the barrel of the syringe. Such secondary compounds include, for instance, one or more antimicrobial compounds including antibacterial compounds, antiviral compounds, and/or antifungal compounds (e.g., coumarin, cinnamic acid, vancomycin, hypericin, iturin-like mycosubtilin, bacillomycin, subtulene A, eumycin, antiviral drugs, clotrimazole, miconazole, ketoconazole, etc.), one or more adjuvants (e.g., aluminum hydroxide, aluminum phosphate, calcium alginate, etc.), one or more dressings and/or coverings (e.g., wound coverings), one or more grafts (e.g., skin grafts or any other type of graft described herein), and the like.

The cover 191 may, in at least one embodiment, be adapted to fit one or more hubs and/or needle tips (e.g., the hub 180 and/or the needle tip 190) such as, for example, needle tips of 51 millimeters (mm)±1 mm in length and associated hubs, needle tips having a length of less than 1 inch (e.g., ½ inch) and associated hubs, needle tips having a length of more than 1 inch (e.g., 1.5 inches) and associated hubs, needle tips of 10-304 mm and associated hubs, metal needle tips and associated hubs, Kel-F needle tips and associated hubs, standard removable needle tips and associated hubs, small gauge removable needle tips and associated hubs, needle tips having one or more gauges between 7 and 33 and associated hubs, and the like. In at least an additional embodiment, the cover 191 is adapted to evacuate one or more materials from one or more portions of the syringe (e.g., liquids, gases, gels, etc.). In at least an additional embodiment, the cover 191 is filled, either entirely or partially, with one or more materials (e.g., inert gases such as helium, argon, krypton, neon, radon, and/or any other noble gas). In at least another embodiment, the cover 191 is configured to fit with, attach on to, and/or connect with, one or more additional hubs (e.g., secondary hubs, tertiary hubs, etc.) associated with one or more additional medical tools and/or medical devices (e.g., additional syringes, drip and/or intravenous (IV) tubes, drip and/or IV bags, tube drippers, infusion apparatuses, cannulas, injectors, beakers, flasks, test tubes, suction tubing, etc.).

As with the hub 180, the cover 191 may be composed of one or more materials, including any one or more of the materials disclosed herein from which the hub 180 are composed. Accordingly, the cover 191 can include one or more plastic polymers (e.g., polypropylene, polyethylene, polycarbonate, thermoplastic elastomers, terephthalate, etc.), one or more resins (e.g., polyactide, starch-filled polypropylene, polyhydroxyalkanoates, etc.), and the like.

It should be appreciated that the syringes described above herein are manual in nature and do not function in an automatic or automated fashion. That is, the above-mentioned syringes require a user to manually operate the syringe (e.g., by depressing the plunger to extrude compounds located inside the barrel of the syringe).

In at least one embodiment of the disclosure, an automated device for applying and/or delivering topical compounds comprises a syringe and a tip portion. Such a tip portion 200 is shown in FIG. 2A in a perspective view. The tip portion 200 can be engaged and/or attached to a syringe via a syringe tip (e.g., tip 176). The tip portion 200 comprises a cap 202 and a membrane 204. The cap 202, which may be hollow in at least one embodiment, comprises a first end, which is the open connector end 206, for engaging and/or attaching (e.g., via a releasable connection) to a syringe (e.g., the syringes 100 and/or 150) via the syringe tip (e.g., the syringe tips 106 and/or 156). The cap 202 further comprises a second end, which is the delivery end 208, disposed opposite to the connector end 206 and fluidly connected to the connector end 206. The cap additionally comprises a cap body 210 disposed between, and connecting, the connector end 206 and the delivery end 208.

The delivery end 208 is further connected to, and may be attached to and/or affixed to, the membrane 204. Such connection may be made by any known mechanism, including, for instance, inserting one end of the membrane into the delivery end.

The connector end may comprise, in at least one embodiment, a luer-style connector. In at least another embodiment, the connector end may comprise any other known connection mechanism, including, for instance, any small-scale and/or small bore fitting for making a leak-free connection (e.g., any fitting for medical devices and/or medical accessories governed by International Organization for Standardization (ISO) standard 80369 or any other similar recognized standard). Non-limiting examples of such connectors and/or connection mechanisms include, for instance, a slip-on connection, a push-on connection, an eccentric tip, a tapered tip, a catheter tip, and combinations thereof. Thus, in at least one embodiment, the device is compatible with, and may be engaged and/or attached to, any syringe tip having one or more of the aforementioned connection mechanisms. The device may further be compatible with, and may be engaged and/or attached to, a tip for any known type of syringe, including, for instance, a disposable syringe, a safety syringe, an insulin syringe, a hypodermic syringe, a multi-shot needle syringe, a venom extraction syringe, an oral syringe, a dental syringe, a dose-sparing syringe, a glass syringe, a plastic syringe (e.g., a polyethylene syringe), and combinations thereof.

Figure 2B:
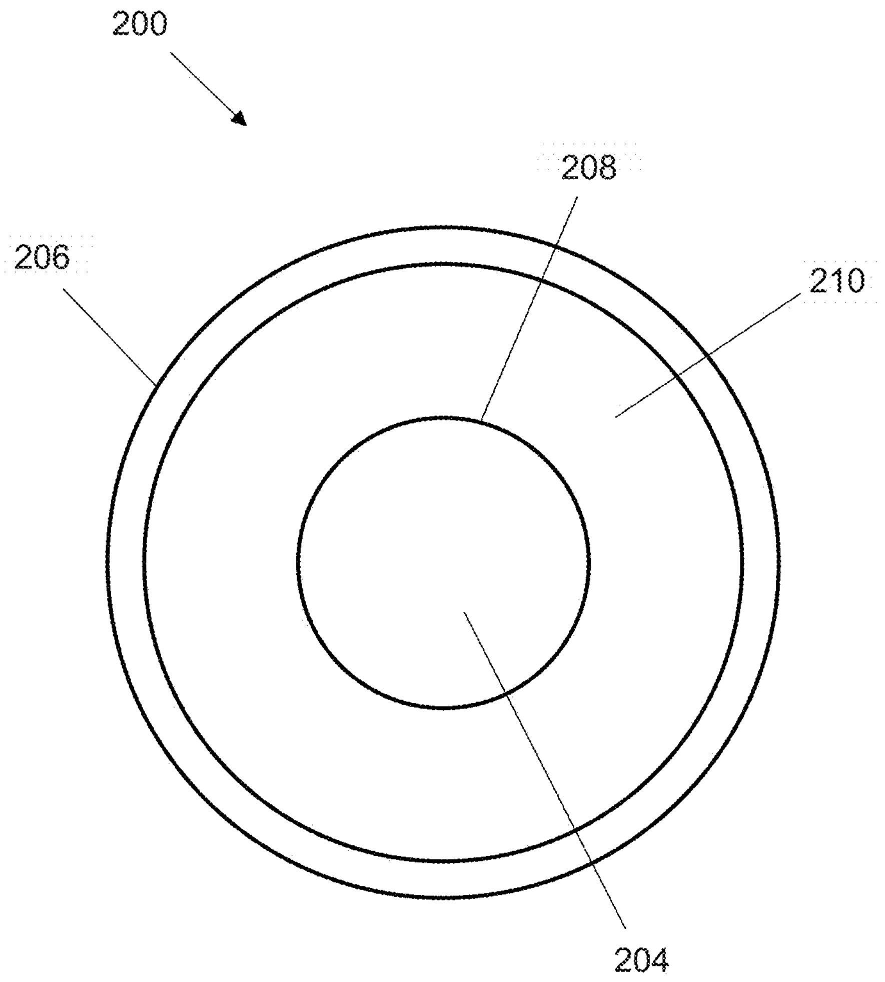

The tip portion 200 is further shown in FIG. 2B in a view from the open connector end 206. An interior surface of the cap body 210 is shown, as is an interior surface of the membrane 204 that is connected to the delivery end 206.

Figure 3A:
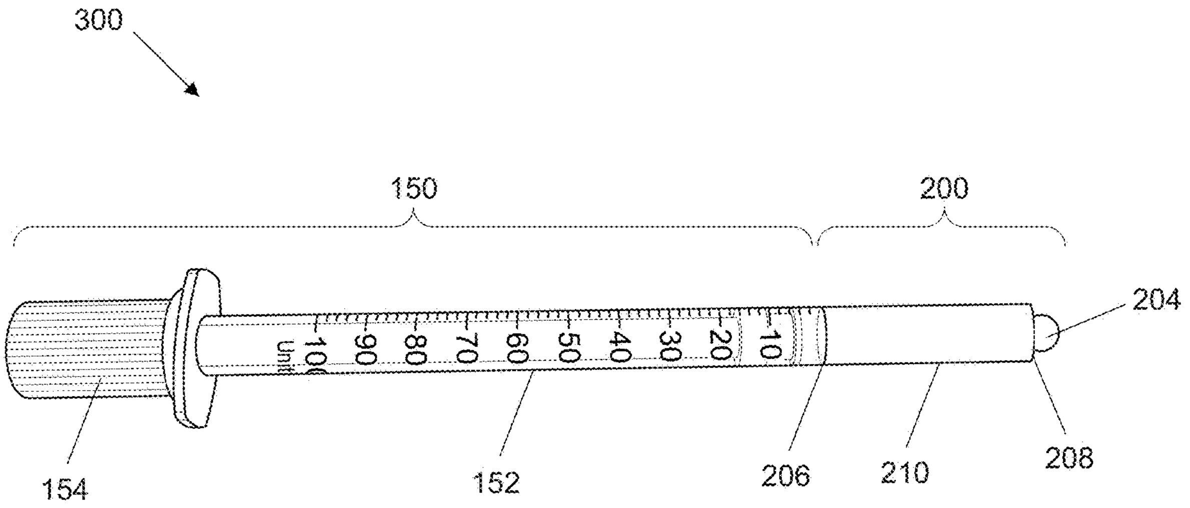
FIGS. 3A-3B show non-limiting examples of syringes, including a syringe with a luer-style connector (FIG. 3B), attached to a device for applying topical compounds, according to at least one embodiment of the present disclosure.

Turning now to FIG. 3A, a device 300 for applying and/or delivering topical compounds, specifically the tip portion 200, is shown connected to a syringe, specifically the syringe 150, via a syringe tip. It should be appreciated that the syringe tip in FIG. 3A is not visible because the tip portion 200, and specifically the connector end 206, is engaged with the syringe tip (e.g., via a releasable connection) such that the device covers the syringe tip and obscures it from view. Further, the connector end 206 is engaged with the syringe tip such that the connector end is fluidly connected to the syringe tip and/or one or more openings in the syringe tip. Thus, as a non-limiting example, the connector end 206 may comprise a luer-style connector that is a lock fitting, in which the connector end screws into threads on the syringe tip, thereby obscuring the syringe tip from view.

When the tip portion is so engaged and/or attached to the syringe tip, one or more compounds (e.g., topical medications) inside the syringe can be introduced from the barrel (e.g., the barrel 152) through the syringe tip (e.g., the syringe tip 156) and through the tip portion, and specifically through the membrane (e.g., the membrane 204) attached to the delivery end of the device, to a surface of a tissue (e.g., skin).

Figure 3B:
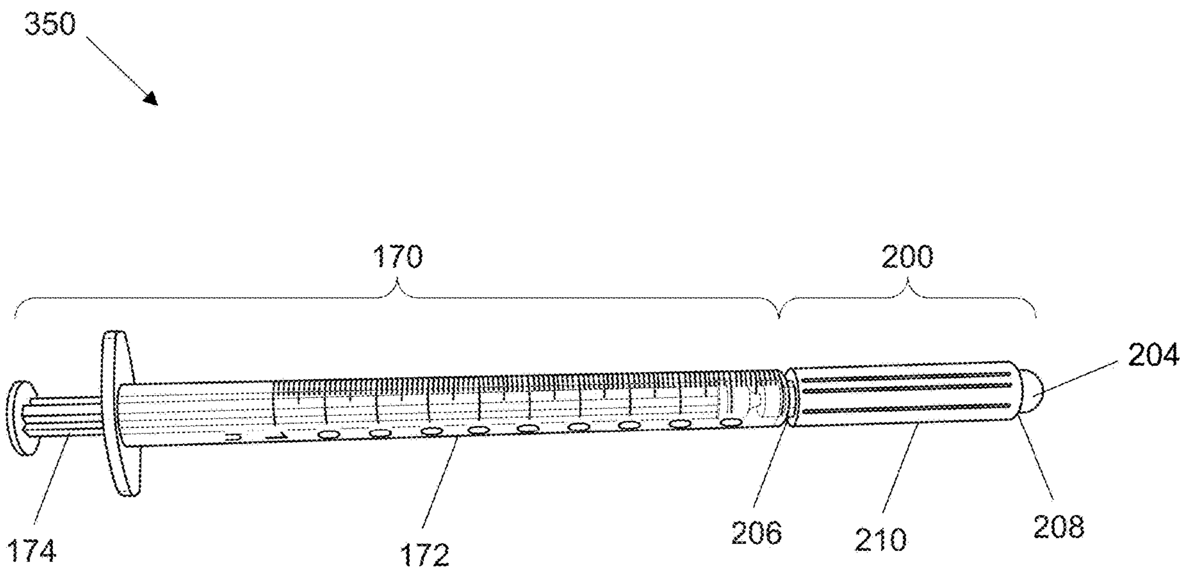

Similarly, FIG. 3B shows a device 350 comprising the tip portion 200 connected to another non-limiting example of a syringe, specifically the syringe 170, via a syringe tip that utilizes a luer-style connector. Again, it should be appreciated that the syringe tip in FIG. 3B is not visible because the tip portion 200, and specifically the connector end 206, is engaged with the syringe tip (e.g., via a luer-style connector) such that the device covers the syringe tip and obscures it from view. Further, the connector end 206 is engaged with the syringe tip, which is a luer-style connector with either a lock fitting or a slip fitting, such that the connector end is fluidly connected to the syringe tip and/or one or more openings in the syringe tip. Accordingly, the connector end 208 obscures the syringe tip from view.

Thus, in at least one embodiment, the tip portion 200 may be used with the syringe 170. When the device is so engaged and/or attached to such a syringe, one or more compounds (e.g., topical medications) inside the syringe can be introduced from the barrel (e.g., the barrel 172) through the syringe tip (e.g., the syringe tip 176, shown in FIG. 1C) and through the device, and specifically through the membrane (e.g., the membrane 204) attached to the delivery end of the device, to a surface of a tissue (e.g., skin).

In at least one embodiment, the membrane is selectively permeable such that the membrane permits the one or more compounds inside the syringe to move through the membrane. It should be appreciated that these selectively permeable properties can be selected based on the biological, chemical, and/or physical nature of the one or more compounds to be delivered to the surface of the tissue. Non-limiting examples of membrane materials include, for instance, one or more polymers (including synthetic/man-made polymers), one or more resins, etc. Thus, the membrane may be composed of, for instance, cellulose, gauze, and the like.

The one or more compounds may be one or more topical medications or other compounds, in any formulation or concentration, including, for instance, triamcinolone, fluorouracil (also known as "5-FU"), tranexamic acid (also known as "TXA"), azelaic acid, one or more bleaching agents (e.g., hydroquinone), one or more topical numbing agents (e.g., lidocaine, bupivacaine), one or more topical antibiotics, one or more dyes or stains (e.g., bonnet blue, gentian violet), one or more topical anti-inflammatory compounds such as nonsteroidal anti-inflammatory drugs (e.g., diclofenac, ibuprofen, Toradol), vitamins (e.g., vitamin A, vitamin B12, vitamin E, vitamin K), one or more topical steroids, one or more topical darkening agents for conditions such as hypopigmented scars (e.g., bimatoprost), anti-oxidants (e.g., N-acetyl-cysteine, glutathione), one or more micro-dosed compounds (e.g., botulinum toxin, hyaluronic acid, other compounds used in micro-needling reservoir treatments), one or more skincare compounds, one or more cosmetic compounds, one or more nutraceutical compounds, and combinations thereof.

Further non-limiting examples of the one or more compounds that could be administered, topically and/or otherwise, through the embodiments described herein include one or more processed human-derived components (e.g., nanofat, platelet-rich plasma (PRP), autogenous materials, and/or allograft materials), one or more types of exosomes, and the like. Each of these will be described briefly below.

Nanofat, in at least some applications, is a bundle of adipose tissue-derived stem cells. Adipose tissue generally contains a heterogenous population of cells, including mesenchymal stromal cells. Adipose-derived cells, including stem cells, can be more easily extracted than other types of stem cells. Further, adipose tissue contains a variety of proteins, such as, for instance, growth factors, transcriptional factors, cytokines, and the like. Accordingly, adipose tissue-derived products can exhibit anti-inflammatory, angiogenesis, and/or immune modulating effects. Such products include, for example, nanofat, microfat, adipose-derived stem cells ("ASC" or "ASCs"), and exosomes, which are described later herein.

Nanofat itself can be produced by, for instance, emulsification and filtration of aspirates from adipose tissue. These aspirates are then physically broken down and/or disintegrated to obtain a product that can be administered to a subject (e.g., via injection, micro-needling, intradermal, subcutaneous, local infiltration, etc.). Generally, nanofat formulations do not contain mature adipocytes (fat cells), but do contain ASCs, various growth factors (e.g., vascular endothelial growth factor (VEGF), platelet-derived growth factor (PDGF), hepatocyte growth factor (HGF), transforming growth factor-beta (TGF-β), and the like), and cytokines (e.g., interleukin (IL)-1RA, IL-4, IL-8, IL-10, IL-13, and the like). Nanofat can therefore be used in regenerative medicine treatments in a variety of medical fields, such as, for example, plastic surgery, dermatology, orthopedics, and the like. In at least one embodiment, the devices, applicators, and/or methods described herein are used to administer one or more formulations containing nanofat for one or more medical treatments, such as, for example, treatment of burns, plastic surgery treatments (e.g., scar reduction), dermatological treatments (e.g., wrinkle reduction, correction of dark eye circles), orthopedic treatments (e.g., regeneration of degenerated and/or diseased cartilage, tendon, and/or ligaments), and combinations thereof.

PRP, which may also be referred to as autologous conditioned plasma, is a product derived from whole blood, which is centrifuged to remove red blood cells. PRP is therefore a concentrate of plasma protein that contains platelets (which may be at, for instance, a concentration 3-5 times that of normal physiological levels), growth factors, cytokines, and other peptides that can stimulate injury repair, tissue healing, wound healing, and tissue rejuvenation. Similar products include, for example, platelet-rich fibrin (PRF). Without wishing to be bound by theory, the concentration of platelets in PRP at a wound or injury site may increase the rate of healing by increasing the rate of tissue repair and/or proliferation. Accordingly, PRP and/or PRF can be used in various medical fields and/or medical treatments, including, for example, dermatology (e.g., skin treatments), orthopedics (e.g., treating muscle strains, tendon injuries, joint injuries, and soft tissue injuries), plastic surgery (e.g., face lifts), and the like. In at least one embodiment, the devices, applicators, and/or methods described herein are used to administer one or more formulations containing PRP and/or PRF for one or more medical treatments, including those described above herein.

Similarly, the devices, applicators, and/or methods described herein may be used to administer one or more formulations containing one or more peptides (e.g., glycoproteins, growth factors such as PDGF and/or TGF-β, cytokines, etc.) and/or one or more cellular materials. Such peptides may be, for instance, derived from PRP or from other human-derived sources (e.g., bone marrow cells). Purely as a non-limiting example, PDGF and TGF-β can participate in one or more injury repair, tissue healing, and/or tissue regeneration processes. Non-limiting examples of the aforementioned one or more cellular materials include one or more types of cells (e.g., adipose cells, blood cells, endothelial cells, epithelial cells, fibroblasts, stem cells, progenitor cells, muscle cells, macrophages and/or other immune cells, etc.), one or more cells that have been genetically engineered and/or modified, bone marrow, lipids, liposomes, vesicles, and combinations thereof.

Further, the devices, applicators, and/or methods described herein may be used to administer one or more formulations containing one or more autogenous materials and/or one or more allograft materials. An "autogenous material" is a material that is taken from the subject or patient's own body. An "allograft material" is a material taken from an individual of the same species as the subject or patient. Both autogenous and allograft materials can be used in a variety of medical treatments, including grafts (e.g., dental grafts, bone grafts). Thus, autogenous and/or allograft materials can be administered to assist in tissue repair, wound healing, and other similar applications. For instance, such materials can be used for treating surgical wounds, deep wounds that include damage of the dermis, eye wounds, dental and oral cavity wounds, internal ulcers (e.g., diabetic, dermal, arterial, venous, and other types of ulcers), burns, scars, and the like.

Additionally, as mentioned above herein, autogenous and/or allograft materials can be used for one or more types of grafts. In at least one embodiment, the devices, applicators, and/or methods described herein may be used to administer a graft. One specific non-limiting example is a skin graft over an open wound, burn, and/or scar. Non-limiting examples of skin and other grafts include autologous skin grafts, allografted skin, artificial skin, autodermic grafts, autoepidermic grafts, dermic grafts, epidermic grafts, avascular grafts, bone grafts, blepharoplastic grafts, cutis grafts, delayed grafts, fascia grafts, full thickness grafts, heterologous grafts, homologous grafts, xenografts, lamellar grafts, mesh grafts, mucosal grafts, patch grafts, pedicle grafts, penetrating grafts, split skin grafts, thick split grafts, and the like.

In at least an additional embodiment, the devices, applicators, and/or methods described herein may be used to administer one or more formulations containing one or more exosomes and/or one or more different types of exosomes. The aforementioned exosomes may be used to treat one or more diseases or conditions; accordingly, the number of exosomes in the one or more formulations can be maximized to be, for instance, 90%, 80%, 70%, 60%, 50%, 40%, or more than 30%. In at least one example, high concentrations of exosomes can be used to treat one or more diseases or conditions (e.g., cancers, tumors, and the like). Such high concentrations can be produced using, for instance, induction of exosomes from stem cells via treatment of these stem cells with cytokines, treatment with liposome stimulation using one or more stimulant liposomes (e.g., neutral or cationic liposomes, see Emam et al., *Biol. Pharm. Bull.* 2018; 41 (5): 733-742), and/or other physical and/or biological methods previously described. See, e.g., Phan et al., *J. Extracell. Vesicles.* 2018; 7 (1): 152223. In at least a further example, the one or more types of exosomes include isolated exosomes, which are exosomes that are physically separated from their natural environment(s). As a non-limiting example, an isolated exosome may be separated from any cells or tissue with which it is naturally associated, including, for instance, various types of stem cells. In at least another example, the one or more types of exosomes include exosomes that are engineered in vitro. This can be achieved through, for example, modifying the cell and/or tissue with which the exosome is naturally associated, exposing such cells and/or tissue to one or more stimulus molecules and/or compounds, and the like.

In at least additional examples, the exosomes administered contain one or more biological compounds. Such compounds may be at a higher level or concentration than the level or concentration present in a naturally occurring exosome (e.g., about 1.5-fold higher, about 3-fold higher, about 10-fold higher, about 20-fold higher, about 50-fold higher, about 100-fold higher, or about 200-fold higher). Non-limiting examples of these compounds include any peptide, any nucleic acid, any lipid, any carbohydrate, osteoinductive factors (e.g., any factor that promotes healing and/or development of bone), neuronal regeneration factors (e.g., any factor that promotes healing and/or regeneration of neurons), immunomodulatory factors (e.g., any factor that influences and/or modulates one or more immune responses and/or immune pathways), extracellular matrix binding factors (e.g., any factor present in the extracellular matrix), extracellular matrix components (e.g., collagen, elastin, fibrin, one or more glycoproteins, one or more proteoglycans, one or more polysaccharides), one or more polymers (e.g., one or more biopolymers), one or more growth factors (e.g., transforming growth factors, platelet-derived growth factors), and one or more micro-RNAs (miRNAs) (e.g., miRNA 218, miRNA 9-5p, miRNA 19a-3p, miRNA 30a-5p, miRNA 212-5p, miRNA 323-5p, miRNA 15a, miRNA 15b, miRNA 16, miRNA 424, miRNA 497, etc.).

One or more compounds described herein can be used to treat a variety of conditions, including, for instance, skin conditions such as scars, burns, hyperpigmentation, inflammation, and/or fibrosis. Purely as non-limiting examples, the device could be used to deliver (1) topical steroids to treat scars, (2) growth factors and anti-scarring medications to treat burns, (3) anti-aging compounds and/or vitamins to improve skin texture, quality, and/or clarity, (4) anti-inflammatory compounds to prevent and/or treat inflammation, and (5) medication or other treatment compounds as part of skin laser treatments, microneedling, dermal abrasion, and the like.

It should also be appreciated that the device may be used to apply one or more topical compounds to mammalian tissues and/or areas other than the skin. For instance, the device can be used to apply one or more compounds (e.g., fibrin-based glues) to nerve conduits, the outside of microvascular anastomosis, the outside of vein grafts, allografts, and/or other grafts, the outside of tendons, acellular dermal matrices, the outside of bone grafts, bone reconstructions, and/or bone substitutes, the outside of the intersections of bone and/or peel and bone substitutes, the outside of bioengineered interfaces and/or bioengineered devices, the outside of implanted devices, and combinations thereof.

Figure 4A:
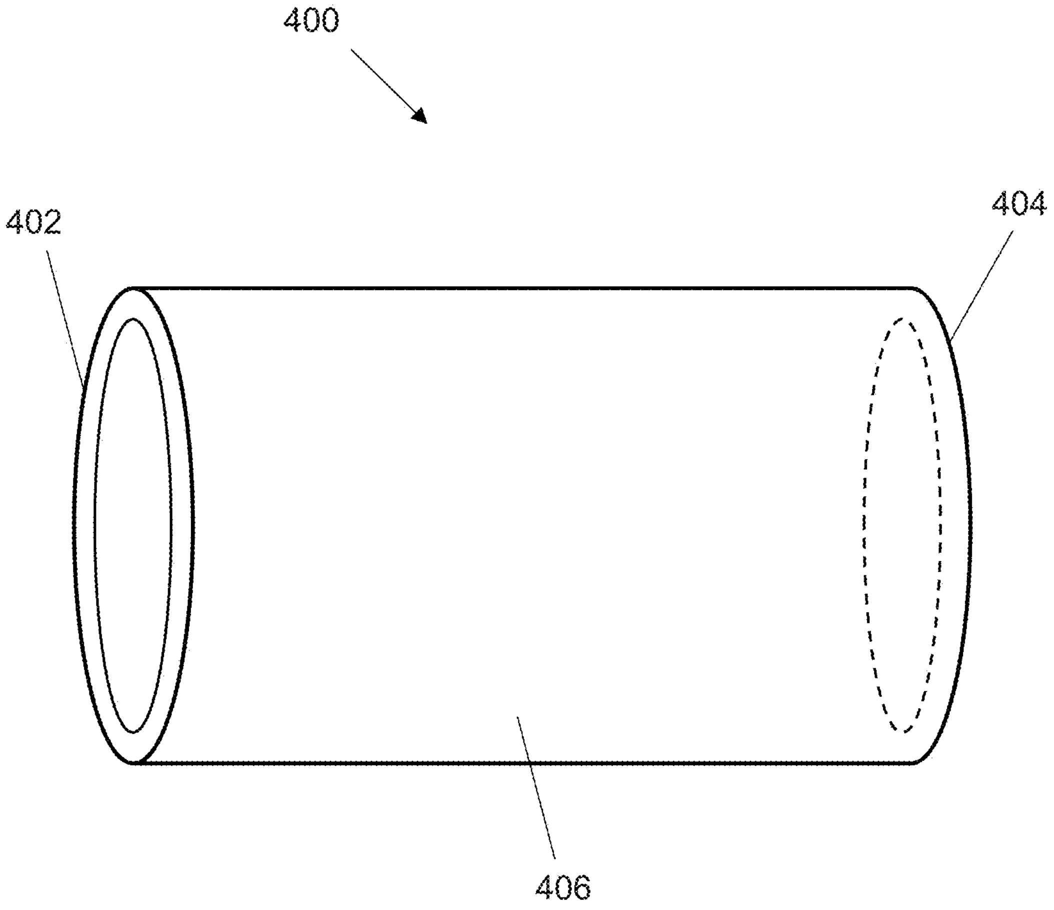
FIGS. 4A-4C show portions of a device for applying topical compounds, specifically, a cap (FIG. 4A), a membrane (FIG. 4B), and a combined cap and membrane (FIG. 4C), according to at least one embodiment of the present disclosure.
Figure 4B:
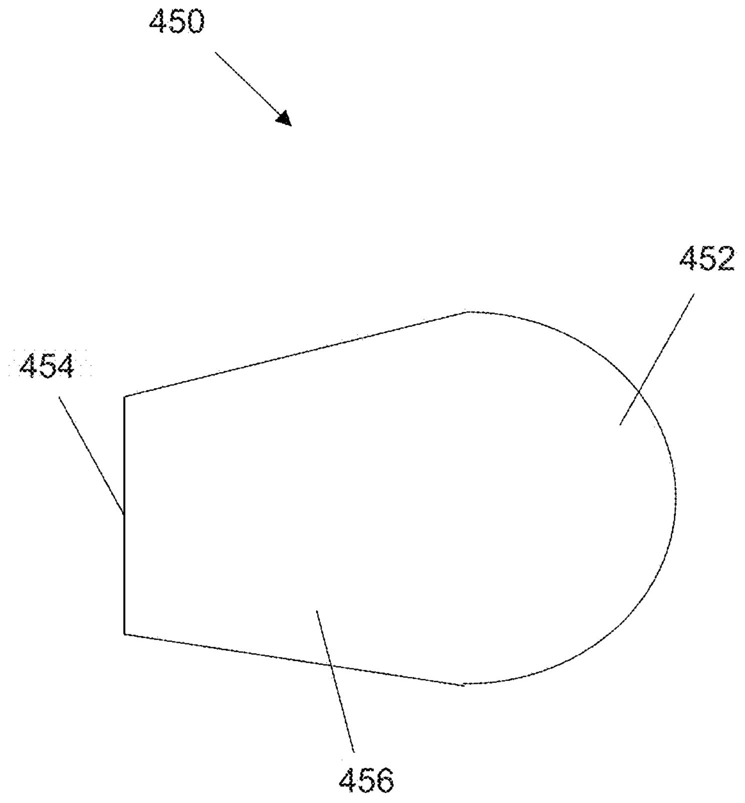

In at least a further embodiment, the device or one or more portions thereof (e.g., the tip portion) can be detachable and/or separable into individual portions, such as, for instance, a cap and a membrane. Thus, FIGS. 4A-4B show a cap 400 (FIG. 4A) that is detachable and/or separate from a membrane 450 (FIG. 4B). The cap 400 may have the same or similar construction as, for instance, the cap 202. The cap 400 comprises an open connector end 402, an open delivery end 404 that is fluidly connected to the open connector end 402, and a cap body 406 disposed between, and connecting, the connector end and the delivery end. It should be appreciated that, in at least one embodiment, the open delivery end 404 can be covered and/or closed with, for instance, a membrane (e.g., the membranes 204, 450).

Turning now to FIG. 4B, the membrane 450 has an outer and/or closed end 452 through which one or more topical compounds can be delivered, an open inner end 454 through which the one or more topical compounds can be introduced into the membrane, and a neck portion 456 connecting the outer and the open inner end. In at least one embodiment, the open inner end 454 of the membrane 450 can be inserted into the open delivery end (e.g., the delivery ends 208, 404) of a cap, such that the open inner end 454 is fluidly connected to the delivery end. Thus, one or more topical compounds introduced into the cap (e.g., when the cap is connected to a syringe tip) flows through the cap from the connector end (e.g., the connector ends 206, 402) to the delivery end and into the membrane via the open inner end 454. The one or more compounds then flow through the neck portion and are extruded out from the outer end 452 on to a surface of mammalian tissue (e.g., skin, mucous membranes, and/or other tissue surfaces).

In at least one embodiment, the open inner end 454 and/or the neck portion 456 are attached to an inner surface of the cap. In at least a further embodiment, the open inner end and/or the neck portion are simply inserted, in a removable fashion, into the cap via the open delivery end (e.g., the delivery ends 208, 404).

Figure 4C:
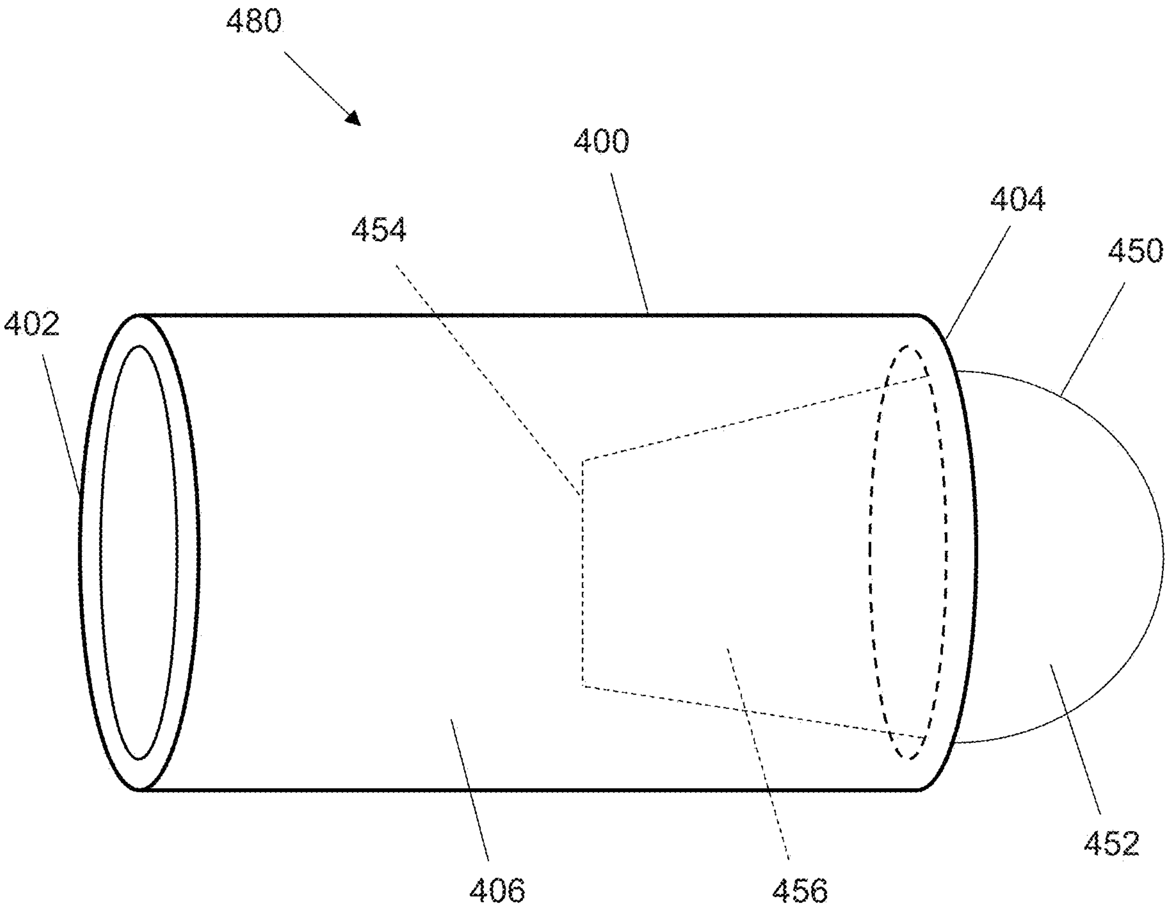

In at least a further embodiment, the membrane 450 can be inserted and/or connected to the cap 400, resulting in a combined cap-membrane device 480, as shown in FIG. 4C. The cap 400 comprises an open connector end 402, a delivery end 404, and a cap body 406. Both the open inner end 454 and the neck portion 456 of the membrane 450 are inserted into the delivery end 404, such that the outer end 452 of the membrane is disposed outside of the delivery end 404.

Thus, like the tip portion 200, the combined cap-membrane device 480 may be engaged and/or attached to a syringe tip (e.g., any of the types of syringe tips described above herein). Specifically, the open connector end 402 can be engaged and/or attached (e.g., via a releasable connection) to such a syringe tip. One or more compounds (e.g., topical medications) inside the syringe can be introduced from the barrel (e.g., the barrels 102, 152) and flow through the syringe tip (e.g., the syringe tips 106, 156) and through the connector end into the cap. The one or more compounds can then flow through the open inner end 454 of the membrane 450, through the neck portion 456, and finally through the outer end 452. The portion of the one or more compounds extruded through the outer end 452 can then be topically applied and/or delivered to the surface of mammalian tissue (e.g., skin, mucous membranes, and/or other tissue surfaces). These one or more compounds may be any of the one or more topical compounds described above herein.

A user (e.g., a medical professional) of at least one embodiment of the device (e.g., the device 300, the device 350, the combined cap-membrane device 480) can apply the one or more compounds inside the syringe (e.g., the syringes 100, 150) to the surface of tissue by holding the syringe as a pen or pencil. The device can then move one or more topical compounds disposed therein (e.g., through membranes 204, 450) to the surface of the tissue. Thus, as a non-limiting example, the aforementioned user could hold the syringe with his or her thumb, forefinger, and/or middle finger.

It should be appreciated that such manner of holding the syringe is in contrast to known methods, in which the user's thumb contacts a top surface of the plunger of the syringe and the user must physically exert force on the plunger to depress the plunger into the barrel, thereby ejecting the one or more compounds inside the barrel through a needle attached to the syringe tip.

It should further be appreciated that holding the syringe as one would a pen or pencil may provide several advantages, especially with respect to the topical application of the one or more compounds, including, for instance, more and/or better control of the amount of the one or more compounds applied, limiting the amount of the one or more compounds applied, more and/or better control of the surface area to which the one or more compounds are applied, prevention of overmedication, prevention of waste, and/or cost savings from avoiding excessive application amounts of the one or more compounds.

In at least one embodiment, the membrane of the device (e.g., the device 300, the device 350, the combined cap-membrane device 480) is additionally pre-coated with one or more topical agents that can be activated by one or more known mechanisms (e.g., via a secondary agent, ultraviolet (UV) light, and the like). A non-limiting example of such topical agents are caged compounds. Generally, caged compounds are compounds that have a photolabile protecting group attached to a molecule or functional group, thereby rendering the entire compound biologically inert. The caged compound can be activated by exposure to one or more types of irradiation (e.g., UV light), which removes the protecting group and releases the molecule or functional group. For instance, nitric oxide compounds can be caged such that, upon exposure to UV light, the nitric oxide (NO) is released. NO may influence and/or participate in a variety of biological processes, including immune responses. NO can also act as an antibacterial and/or antiviral compound by, for instance, rupturing the plasma membrane of bacteria and/or viruses. Accordingly, in at least one embodiment, the membrane of a device as described herein is pre-coated with a caged compound (e.g., a caged nitric oxide compound) that is then activated by exposure to UV light. In the case of a caged nitric oxide compound, NO is then released, which can then be administered to a subject.

In at least a further embodiment, one or more devices described herein can be used to administer one or more caged compounds that release a primary medicament and/or a secondary medicament in a temporally controlled fashion via controlled exposure to UV light. Such medicaments, which can be compounds that are used for one or more medical treatments, include, for example, drugs, prodrugs, signaling molecules, secondary messengers, neurotransmitters, inositols, calcium, capsaicin, nucleosides, nucleotides, peptides, enzymes, nucleic acids, antibacterial compounds, antiviral compounds, and the like.

Figure 5A:
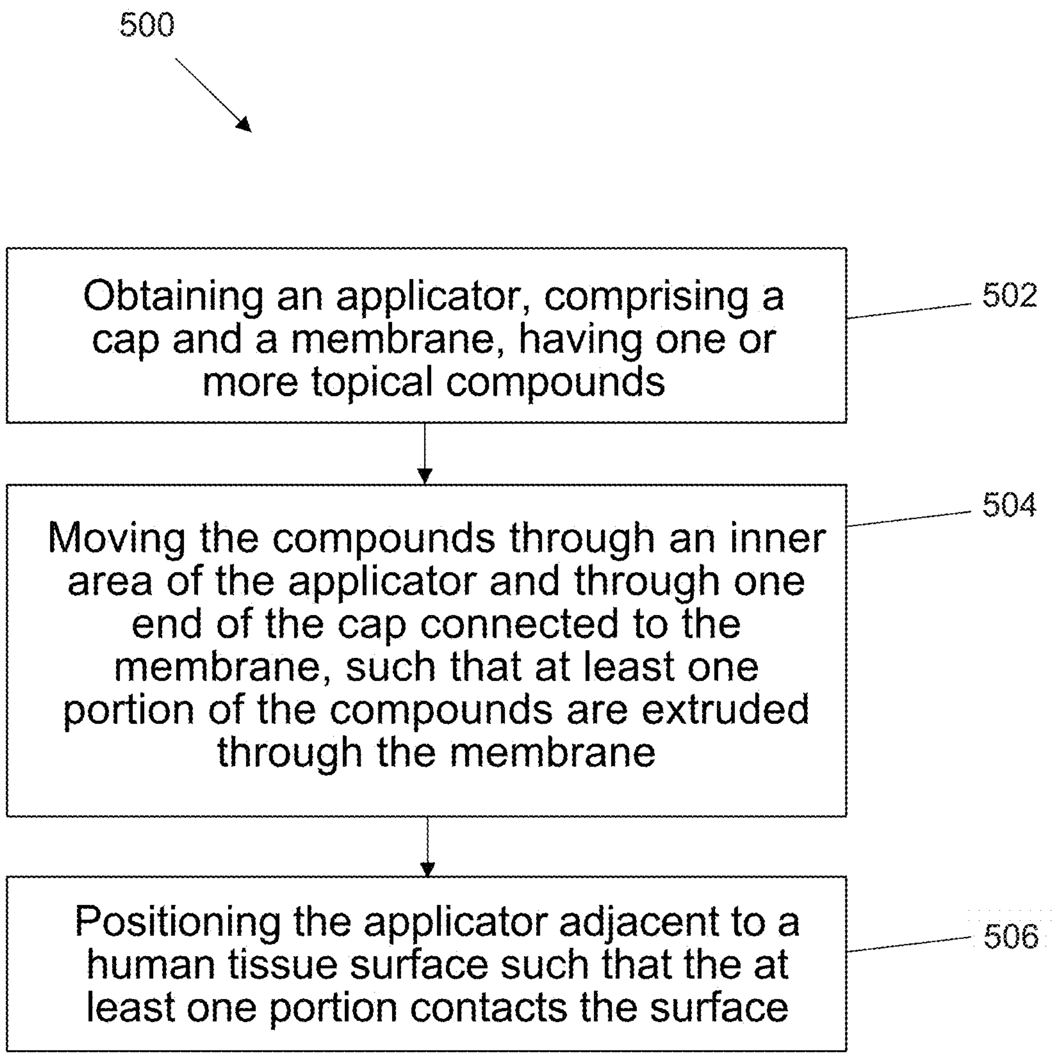
FIGS. 5A-5C are flow diagrams showing a method for delivering one or more topical compounds, according to at least one embodiment of the present disclosure.

Turning now to FIG. 5, a method 500 for delivering one or more topical compounds is also disclosed herein. The method 500 comprises obtaining, at a block 502, an applicator having one or more topical compounds to be delivered, the applicator comprising a cap and a membrane, the cap comprising one end connected to the membrane, the cap comprising an inner area; moving, at a block 504, the one or more topical compounds through the inner area of the applicator and through the one end, such that at least one portion of the one or more topical compounds are extruded through the membrane; and positioning, at a block 506, the applicator adjacent to a surface of mammalian tissue such that the at least one portion of the one or more topical compounds contacts the surface, thereby delivering the one or more topical compounds.

In at least a further embodiment, the applicator comprises a syringe, which may be any syringe described above herein. The syringe comprises a barrel and a syringe tip, which may be any syringe tip described above herein. The cap may further comprise a connector end (e.g., any of the connector ends described above herein) that is configured to attach (e.g., via a releasable connection) to the syringe tip. Additionally, the aforementioned one end may be, for instance, any of the delivery ends described above herein.

Figure 5B:
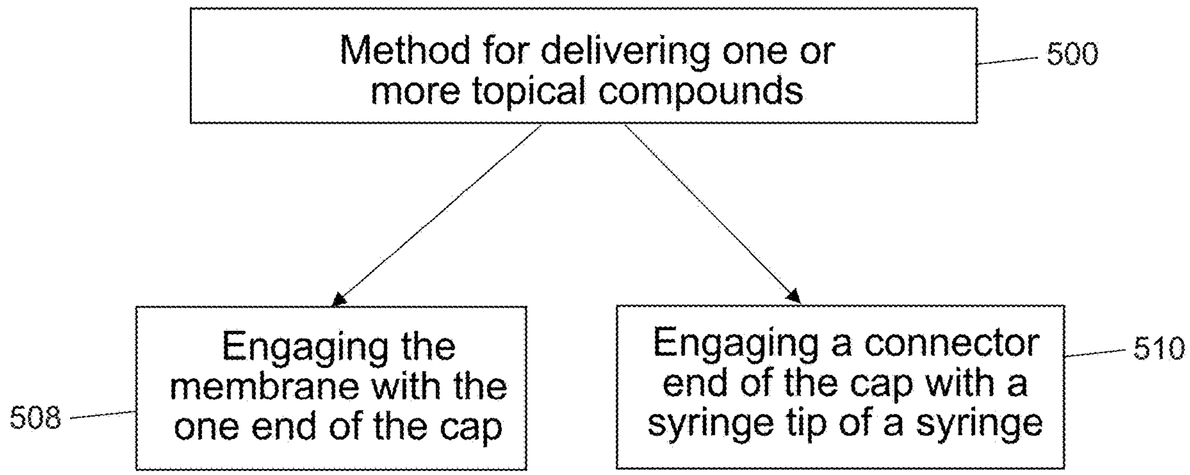

Thus, as shown in FIG. 5B, the method 500 may further comprise engaging, at a block 508, the membrane with the one end of the cap; and/or engaging, at a block 510, the connector end of the cap with a syringe tip of a syringe.

Figure 5C:
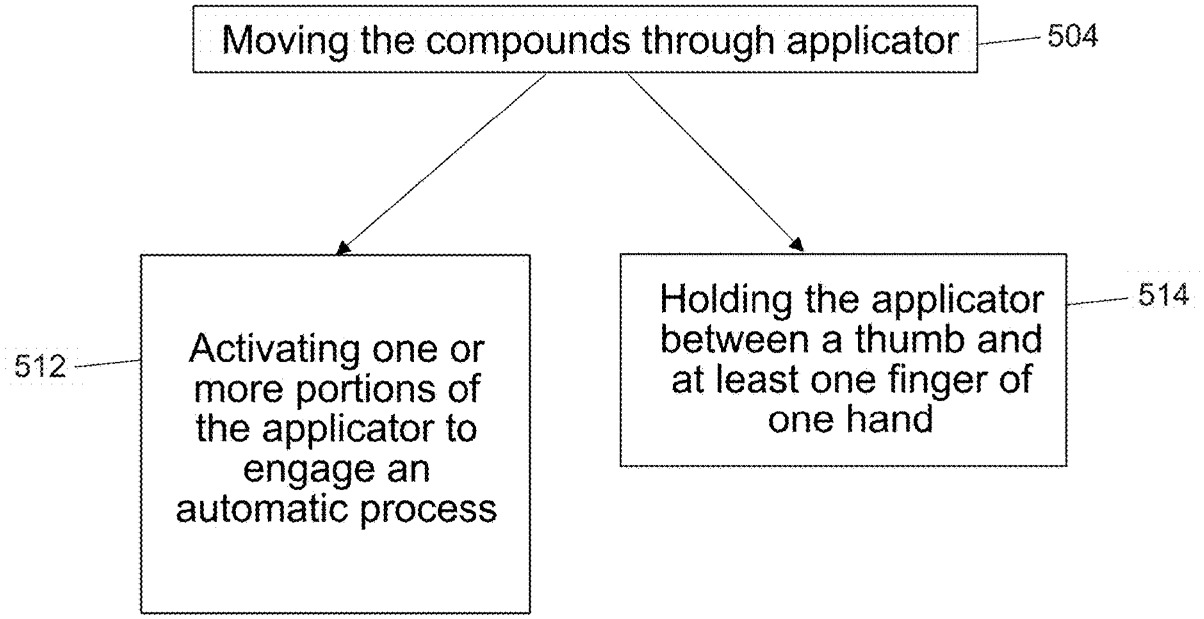

Further, as shown in FIG. 5C, the aforementioned moving step at the block 504 may further comprise activating, at a block 512, one or more portions of the applicator to engage an automatic and/or automated process to move the one or more topical compounds through the syringe tip and through the connector end. The moving step may additionally comprise holding, at a block 514, the applicator between a thumb and at least one finger of one hand. A skilled artisan will appreciate that a user of the method may hold the applicator in such fashion to provide one or more benefits, as mentioned above herein, when compared with using the thumb to exert force on the syringe plunger to depress the plunger into the barrel, thereby ejecting the one or more compounds inside the barrel through a needle attached to the syringe tip.

The aforementioned one or more topical compounds in the applicator may be any of the compounds described above herein, including, for instance, triamcinolone, fluorouracil (also known as "5-FU"), tranexamic acid (also known as "TXA"), azelaic acid, one or more bleaching agents (e.g., hydroquinone), one or more topical numbing agents (e.g., lidocaine, bupivacaine), one or more topical antibiotics, one or more dyes or stains (e.g., bonnet blue, gentian violet), one or more topical anti-inflammatory compounds such as nonsteroidal anti-inflammatory drugs (e.g., diclofenac, ibuprofen, Toradol), vitamins (e.g., vitamin A, vitamin B12, vitamin E, vitamin K), one or more topical steroids, one or more topical darkening agents for conditions such as hypopigmented scars (e.g., bimatoprost), anti-oxidants (e.g., N-acetyl-cysteine, glutathione), one or more micro-dosed compounds (e.g., botulinum toxin, hyaluronic acid, other compounds used in micro-needling reservoir treatments), one or more skincare compounds, one or more cosmetic compounds, one or more nutraceutical compounds, and combinations thereof.

As stated above herein, at least one embodiment of the device is partially or completely automated and/or automatic. Specifically, any of the devices described above herein (e.g., the device 300, the device 350, the combined cap-membrane device 480) may be partially or completely automated and/or automatic. Further non-limiting examples of such automation and/or automated functions are described in further detail below and one or more aspects thereof may be combinable. For instance, specific automated aspects, such as automated tabs, levers, and/or buttons, may be combined with specific other automated aspects (e.g., automated loading of the topical compounds). It should be appreciated that any of the automated devices described herein may apply and/or deliver any of the topical compounds described herein.

Figure 6:
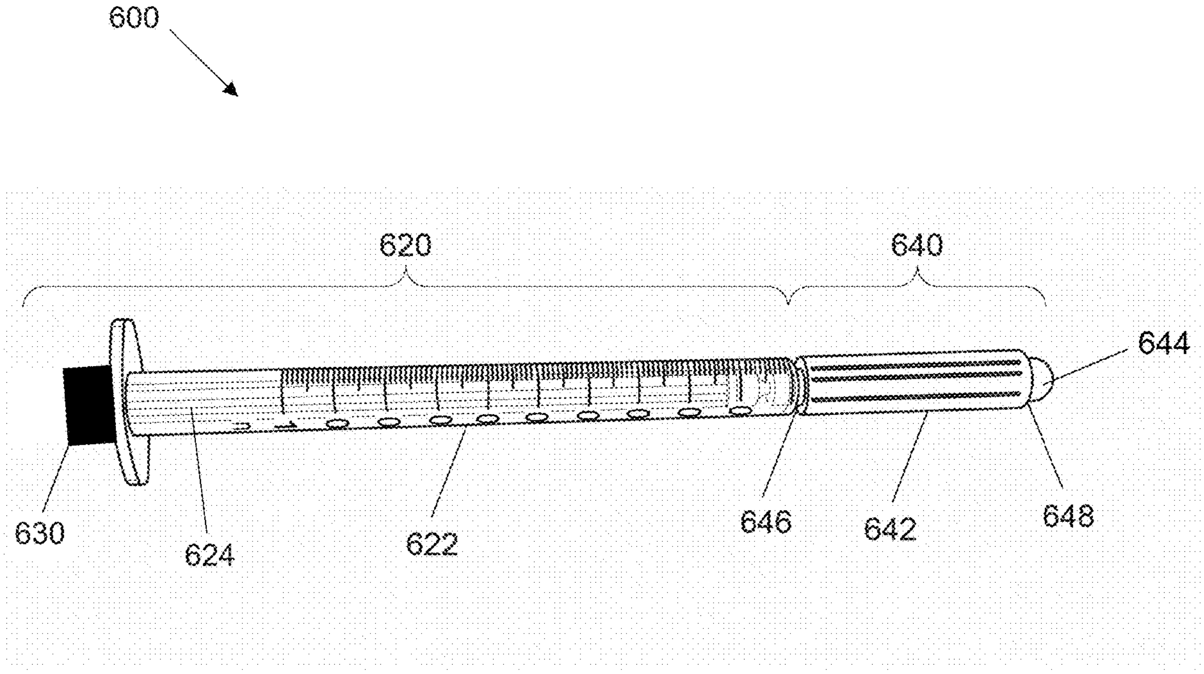
FIG. 6 shows an automated device for applying and/or delivering topical compounds, the device having a portion that can be physically manipulated to automatically move a plunger, according to at least one embodiment of the present disclosure.

Turning now to FIG. 6, an automated device 600 for applying and/or delivering topical compounds is shown. The device 600 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. Additionally, the device 600 comprises a top portion 630 that can be physically manipulated (e.g., moved, pressed, depressed, etc.) by a user to trigger automatic movement of the plunger 624. The top portion 630 can be of any physically manipulatable construction (e.g., a tab, a lever, a button, etc.). It should be appreciated that the top portion may be used with any automated device described herein, and is not limited to the specific embodiment shown. Further, the top portion may be used in combination with any one or more embodiments described below herein. In at least one example, manipulation of the top portion 630 results in the plunger 624 moving partially through the barrel or chamber 622, in order to deliver a pre-measured and/or pre-determined amount of the topical compounds inside the automated device 600 (e.g., through the tip portion 640 and/or one or more portions thereof, including, for instance, the delivery end 648 and/or the membrane 644, to deliver and/or apply the topical compounds to a surface of human tissue). The pre-measured and/or pre-determined amount may, in at least one example, be one or more specific doses and/or applications of the topical compounds. In at least another example, manipulation of the top portion 630 results in the plunger 624 moving completely through the barrel or chamber 622 (e.g., to an end of the barrel adjacent to the connector 646), in order to deliver all, or substantially all, of the topical compounds inside the automated device 600 (e.g., through the tip portion 640 and/or one or more portions thereof, including, for instance, the delivery end 648 and/or the membrane 644, to deliver and/or apply the topical compounds to a surface of human tissue). In at least one example, the plunger 624 is therefore not manual and/or cannot be manually operated, but rather operates in an automated fashion upon physical manipulation of the top portion 630. In at least another example, the plunger 624 can be manually operated in situations in which the top portion 630 is not usable (e.g., in the event of a malfunction of the automated top portion 624).

Figure 7:
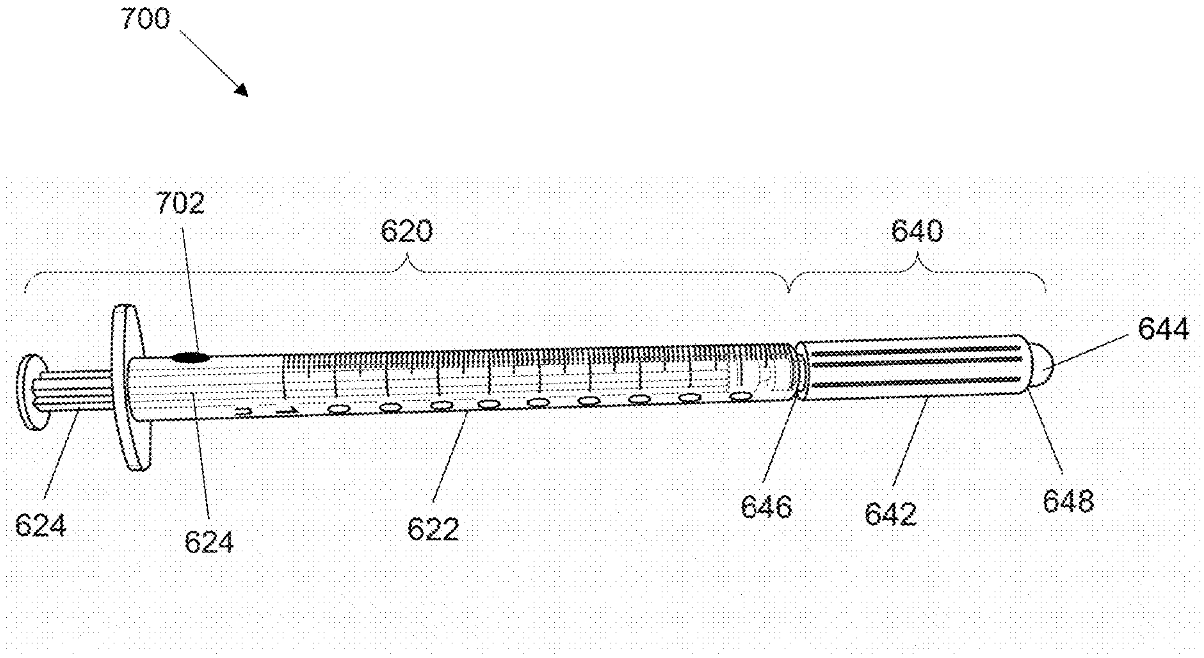
FIG. 7 shows an automated device for applying and/or delivering topical compounds, the device having an area disposed on a side of the device that can be physically manipulated to automatically move a plunger, according to at least one embodiment of the present disclosure.

Turning now to FIG. 7, an automated device 700 for applying and/or delivering topical compounds is shown. The device 700 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The syringe 620 further comprises an area 702, disposed on a side of the barrel or chamber 622, that can be physically manipulated (e.g., moved, pressed, depressed, etc.) by a user to trigger automatic movement of the plunger 624. The area 702 can be of any physically manipulatable construction (e.g., a tab, a lever, a button, etc.) and can be disposed anywhere on the device 700. It should be appreciated that the area 702 may be used with any automated device described herein, and is not limited to the specific embodiment shown. Further, the area 702 may be used in combination with any one or more embodiments described below herein. In at least one example, manipulation of the area 702 results in the plunger 624 moving partially through the barrel or chamber 622, in order to deliver a pre-measured and/or pre-determined amount of the topical compounds inside the automated device 700 (e.g., through the tip portion 640 and/or one or more portions thereof, including, for instance, the delivery end 648 and/or the membrane 644, to deliver and/or apply the topical compounds to a surface of human tissue). The pre-measured and/or pre-determined amount may, in at least one example, be one or more specific doses and/or applications of the topical compounds. In at least another example, manipulation of the area 702 results in the plunger 624 moving completely through the barrel or chamber 622 (e.g., to an end of the barrel adjacent to the connector 646), in order to deliver all, or substantially all, of the topical compounds inside the automated device 700 (e.g., through the tip portion 640 and/or one or more portions thereof, including, for instance, the delivery end 648 and/or the membrane 644, to deliver and/or apply the topical compounds to a surface of human tissue). In at least one example, the plunger 624 is therefore not manual and/or cannot be manually operated, but rather operates in an automated fashion upon physical manipulation of the area 702. In at least another example, the plunger 624 can be manually operated in situations in which the area 702 is not usable (e.g., in the event of a malfunction of the area 702).

Figure 8:
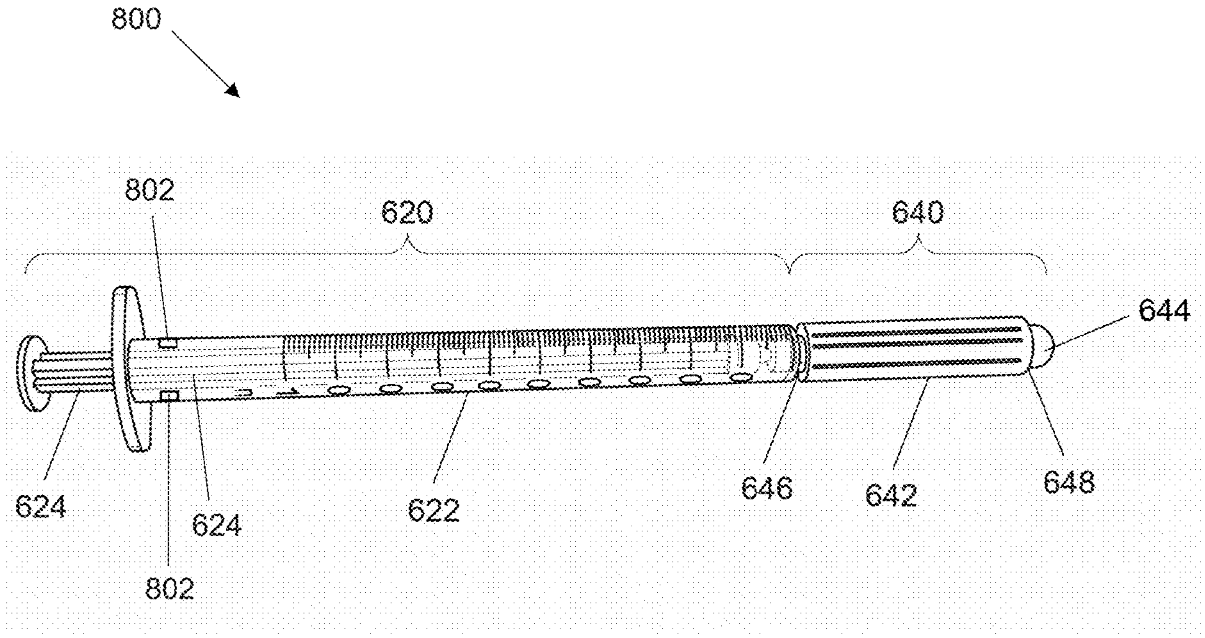
FIG. 8 shows an automated device for applying and/or delivering topical compounds, the device having a plunger that operates under electric power, according to at least one embodiment of the present disclosure.

Turning now to FIG. 8, an automated device 800 for applying and/or delivering topical compounds is shown. The device 800 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 800 or one or more portions thereof (e.g., the syringe 620 or one or more portions thereof) is automated such that the plunger 624 operates under electric power. In at least one example, batteries 802 are disposed inside the barrel or chamber 622 and provide such electric power to move the plunger 624. In at least another embodiment, provision of electric power is provided by a charger and/or charging device that can be plugged into a power socket. It should be appreciated that movement of the plunger 624 under electric power (e.g., via batteries 802) may be used with any automated device described herein, and is not limited to the specific embodiment shown. Further, movement of the plunger 624 under electric power (e.g., via batteries 802) may be used in combination with any one or more embodiments described below herein. In at least one example, the plunger 624 operates under electric power (e.g., via batteries 802) to move partially through the barrel or chamber 622, in order to deliver a pre-measured and/or pre-determined amount of the topical compounds inside the automated device 800 (e.g., through the tip portion 640 and/or one or more portions thereof, including, for instance, the delivery end 648 and/or the membrane 644, to deliver and/or apply the topical compounds to a surface of human tissue). The pre-measured and/or pre-determined amount may, in at least one example, be one or more specific doses and/or applications of the topical compounds. In at least another example, the plunger 624 operates under electric power (e.g., via batteries 802) to move completely through the barrel or chamber 622 (e.g., to an end of the barrel adjacent to the connector 646), in order to deliver all, or substantially all, of the topical compounds inside the automated device 800 (e.g., through the tip portion 640 and/or one or more portions thereof, including, for instance, the delivery end 648 and/or the membrane 644, to deliver and/or apply the topical compounds to a surface of human tissue).

Figure 9:
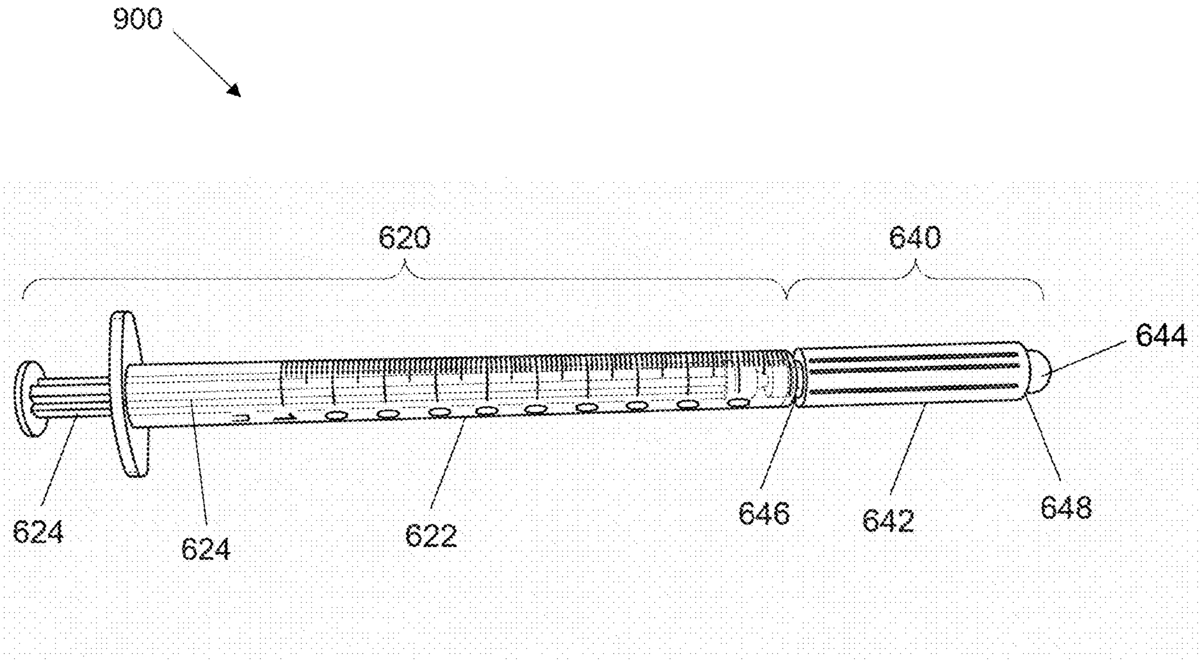
FIG. 9 shows an automated device for applying and/or delivering topical compounds, the device having an automated connector between a syringe portion and a tip portion, according to at least one embodiment of the present disclosure.

Turning now to FIG. 9, an automated device 900 for applying and/or delivering topical compounds is shown. The device 900 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The connector 646 may be automated such that attachment between the syringe 620 and the tip portion 640 is automatic. In at least one example, a user can bring the syringe 620 into contact with the tip portion 640, whereupon attachment via the connector 646 is automatic (or, alternatively, via physical manipulation of a tab, button, and/or lever disposed anywhere on the device 900). In at least another example, removal of the tip portion 640 from physical connection and/or attachment with the syringe 620 is achieved via the automated connector 646 (e.g., after the topical compounds have been delivered and/or administered, and/or when the tip portion 640 must be changed). Such detachment may occur automatically after depressing the plunger 624 a pre-determined or pre-set distance, or, alternatively or additionally, after the plunger 624 has been depressed an entire distance down the barrel 622. Detachment may also occur via physical manipulation of a tab, button, and/or lever disposed anywhere on the device 900. It should be appreciated that such automatic attachment and/or detachment via connector 646 may be used with any automated device described herein, and is not limited to the specific embodiment shown. Further, automatic attachment and/or detachment via connector 646 may be used in combination with any one or more embodiments described below herein.

Figure 10:
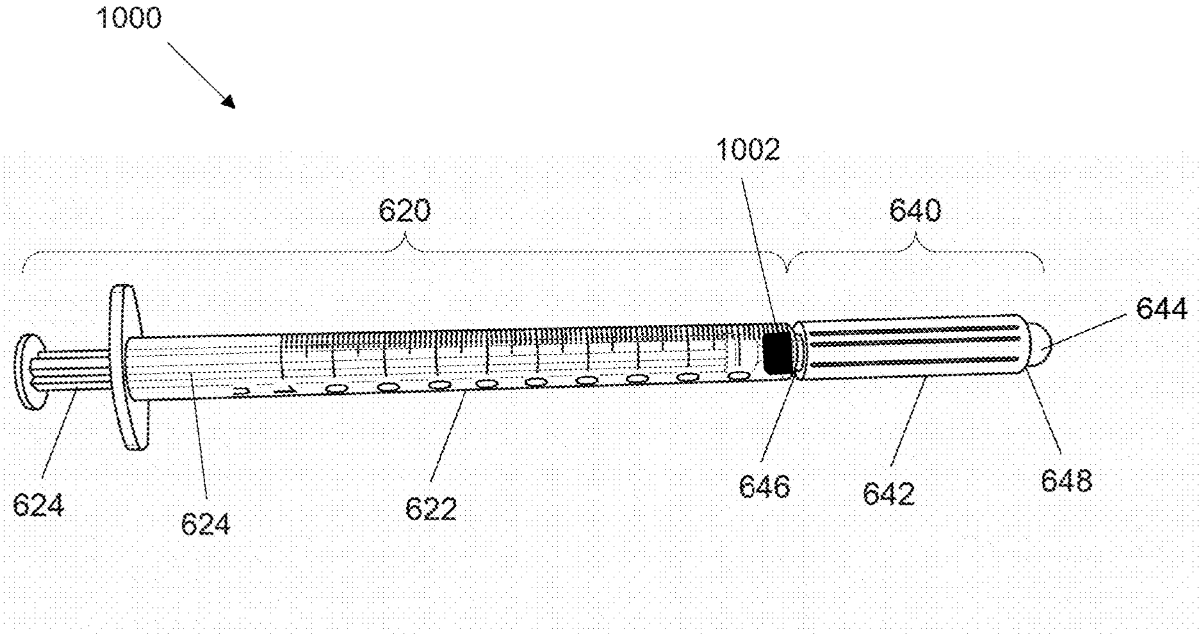
FIG. 10 shows an automated device for applying and/or delivering topical compounds, the device having a capsule that automatically releases the topical compounds according to at least one embodiment of the present disclosure.

Turning now to FIG. 10, an automated device 1000 for applying and/or delivering topical compounds is shown. The device 1000 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The syringe 620 further comprises a capsule 1002 that contains a pre-measured and/or pre-determined amount of one or more topical compounds to be delivered and/or administered. The capsule 1002 can be inserted into an interior of the barrel or chamber 622. In at least one example, depression of the plunger 622 such that it contacts the capsule 1002 results in puncture of the capsule and/or release of the topical compounds contained within the capsule. This results in the topical compounds filling at least a portion of the barrel or chamber 622 such that the topical compounds can then be delivered and/or administered (e.g., through the tip portion 640). It should be appreciated that such a capsule 1002 may be used with any automated device described herein, and is not limited to the specific embodiment shown. Further, the capsule 1002 may be used in combination with any one or more embodiments described below herein.

Figure 11:
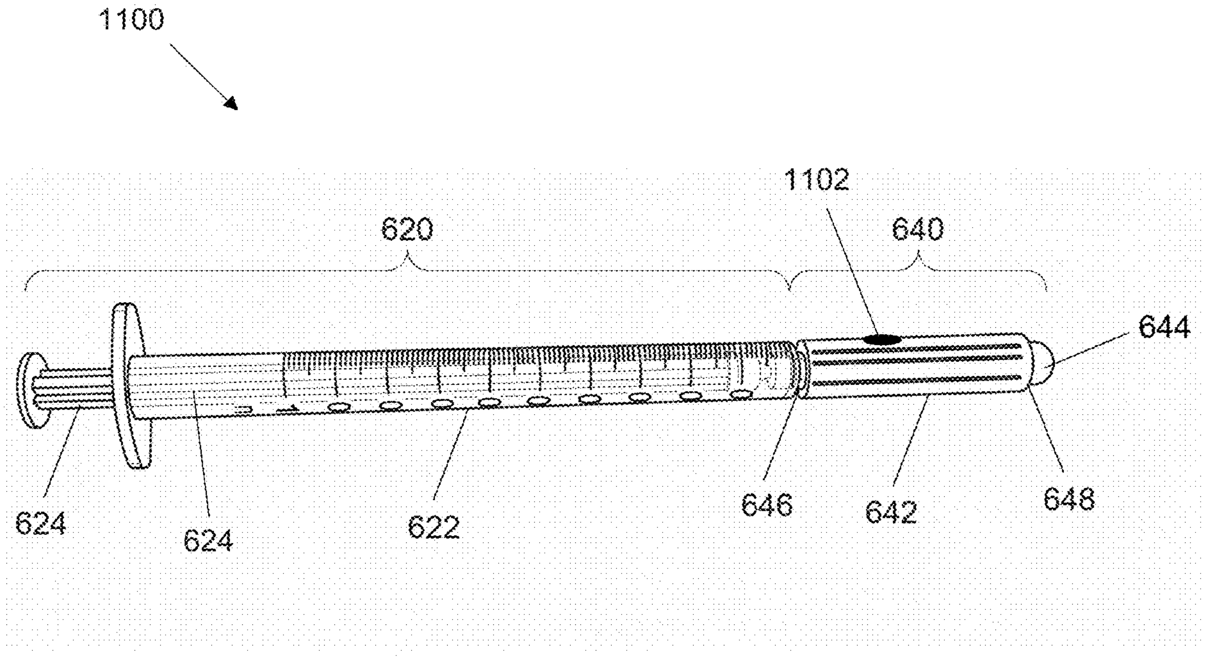
FIG. 11 shows an automated device for applying and/or delivering topical compounds, the device having an area that can be physically manipulated to automatically move the topical compounds from a syringe portion into a tip portion, according to at least one embodiment of the present disclosure.

Turning now to FIG. 11, an automated device 1100 for applying and/or delivering topical compounds is shown. The device 1100 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The tip portion 640 can be automatically loaded with at least a portion of the one or more topical compounds via area 1102. The area 1102 can be physically manipulated (e.g., moved, pressed, depressed, etc.) by a user to trigger automatic loading of one or more portions of the topical compounds from the syringe 620 into the tip portion 640, without the one or more portions being released out of the membrane 644. In other words, in at least one example, one or more portions of the topical compound can be moved into the tip portion 640 in preparation for delivery and/or administration to a surface of human tissue (e.g., skin). The area 1102 can be of any physically manipulatable construction (e.g., a tab, a lever, a button, etc.) and can be disposed anywhere on the device 1100. It should be appreciated that the area 1102 may be used with any automated device described herein, and is not limited to the specific embodiment shown. Further, the area 1102 may be used in combination with any one or more embodiments described below herein.

Figure 12:
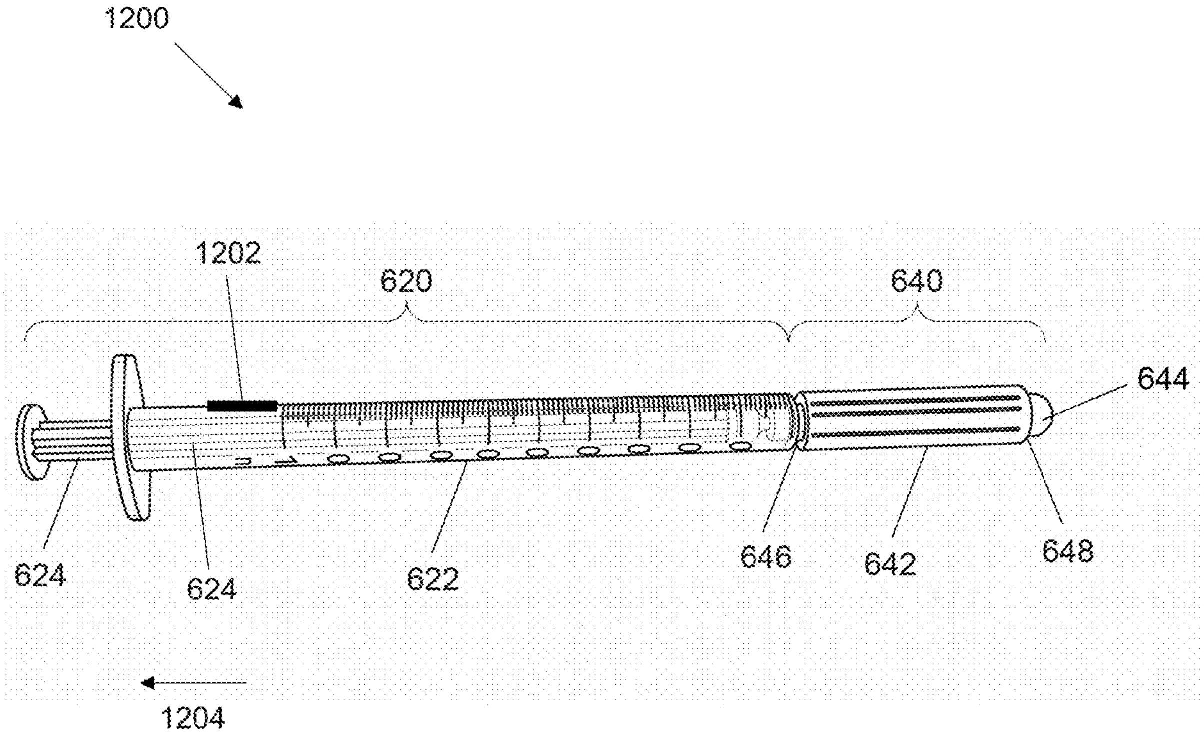
FIG. 12 shows an automated device for applying and/or delivering topical compounds, the device having an area that can be physically manipulated to automatically aspirate a liquid into the device, according to at least one embodiment of the present disclosure.

Turning now to FIG. 12, an automated device 1200 for applying and/or delivering topical compounds is shown. The device 1200 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 1200 can be automated such that liquid can be aspirated through the membrane 644 back into the tip portion 640 and/or the syringe 620. Such liquid may be, in at least one example, any amount of the topical compounds that have accidentally spilled or are required to be aspirated back into the device 1200. Area 1202 can be physically manipulated (e.g., moved, pressed, depressed, etc.) by a user to trigger the aforementioned automatic aspiration, in which plunger 622 can move in direction 1204. Such movement results in aspiration of a fluid or liquid back through the tip portion 640 and/or the syringe 620. The area 1202 can be of any physically manipulatable construction (e.g., a tab, a lever, a button, etc.) and can be disposed anywhere on the device 1200. It should be appreciated that the area 1202 may be used with any automated device described herein, and is not limited to the specific embodiment shown. Further, the area 1202 may be used in combination with any one or more embodiments described below herein.

Figure 13:
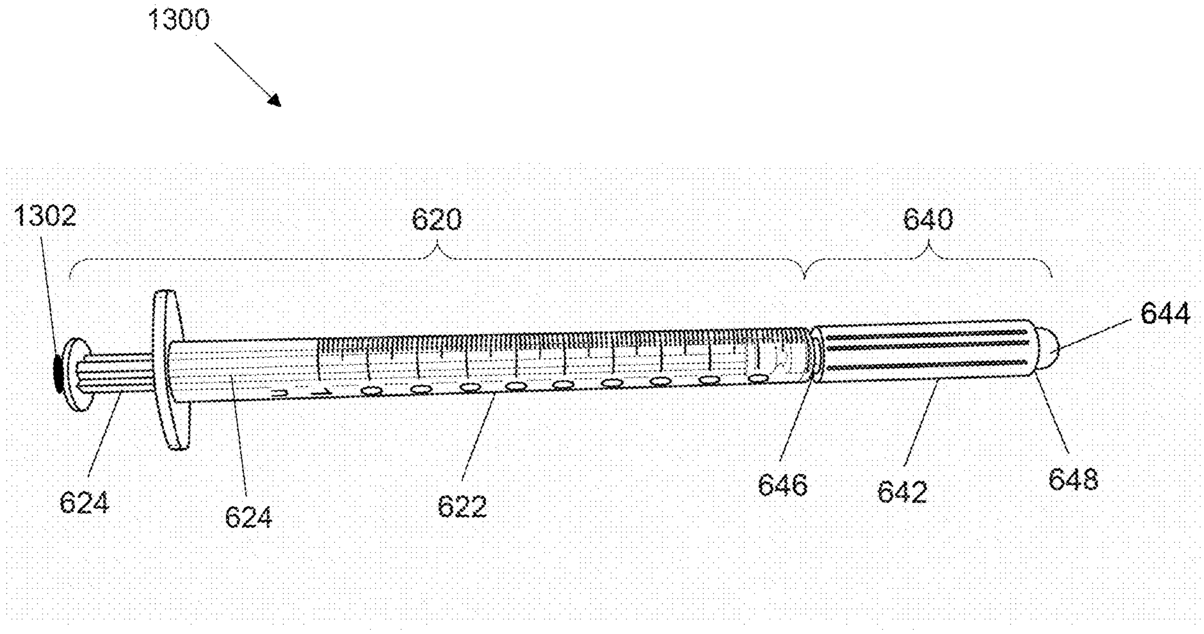
FIG. 13 shows an automated device for applying and/or delivering topical compounds, the device having an area that can be physically manipulated to automatically expel any air inside the device, according to at least one embodiment of the present disclosure.

Turning now to FIG. 13, an automated device 1300 for applying and/or delivering topical compounds is shown. The device 1300 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 1300 can be automated in order to remove any air in the barrel or chamber 622 before delivery and/or administration of the topical compounds (e.g., before placement of the topical compounds within the barrel or chamber). Area 1302 can be physically manipulated (e.g., moved, pressed, depressed, etc.) by a user to trigger the aforementioned automatic air removal, in which plunger 622 can be fully depressed within the interior of the barrel or chamber 622 to expel any air in the barrel or chamber. The area 1302 can be of any physically manipulatable construction (e.g., a tab, a lever, a button, etc.) and can be disposed anywhere on the device 1300. It should be appreciated that the area 1302 may be used with any automated device described herein, and is not limited to the specific embodiment shown. Further, the area 1302 may be used in combination with any one or more embodiments described below herein.

Figure 14:
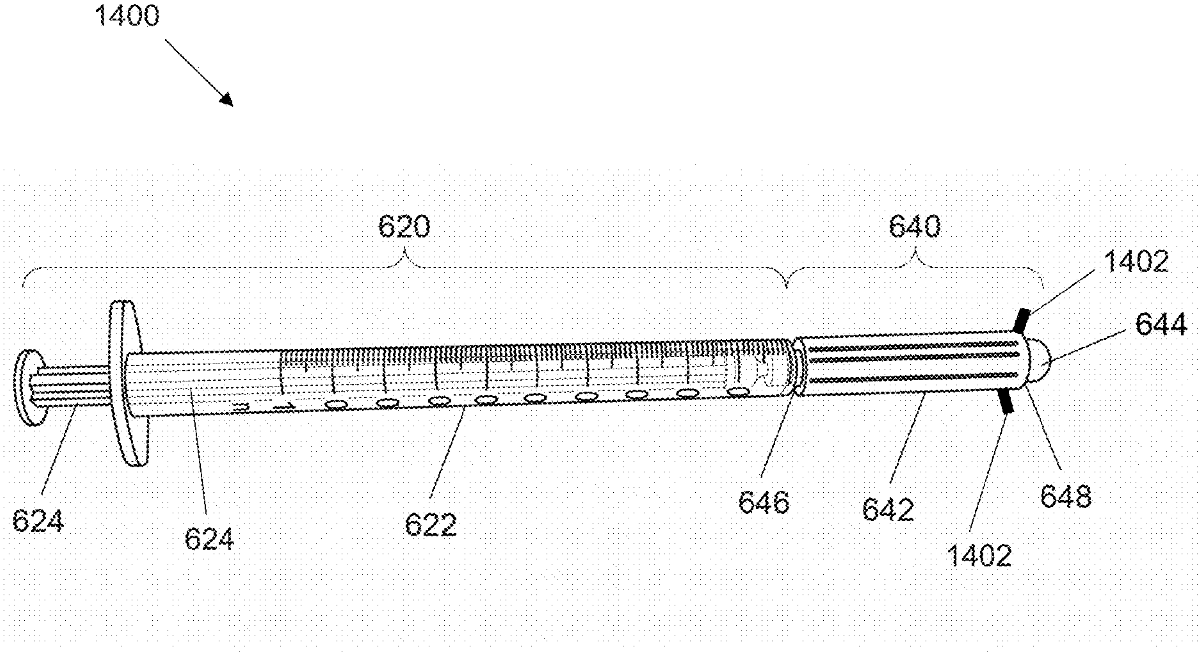
FIG. 14 shows an automated device for applying and/or delivering topical compounds, the device having automated sensors, according to at least one embodiment of the present disclosure.

Turning now to FIG. 14, an automated device 1400 for applying and/or delivering topical compounds is shown. The device 1400 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 1400 can further comprise automated sensors 1402 that detect a distance and/or proximity of the device or one or more portions thereof (e.g., the membrane 644) to a surface of human tissue (e.g., skin). This can assist with more accurate administration, including, for instance, detecting if the device 1400 or one or more portions thereof are touching the surface of human tissue and/or at a predetermined distance from the surface. It should be appreciated that the sensors 1402 may be used with any automated device described herein, and is not limited to the specific embodiment shown. Further, the sensors 1402 may be used in combination with any one or more embodiments described below herein.

In at least one example, the sensors activate an automated alarm or other notification (e.g., an audio alarm, a visual light, and the like) to notify a user to prevent improper use and/or misuse of the device. In at least another example, the automated alarm activates to prevent slippage of the plunger 624 in the barrel or chamber 622 when depressing the plunger to administer the one or more topical compounds. In at least another example, the automated alarm activates to prevent improper removal and/or pull out of the plunger 624 while topical compounds remain inside the barrel or chamber 622 (e.g., to avoid spillage of the topical compounds).

Figure 15:
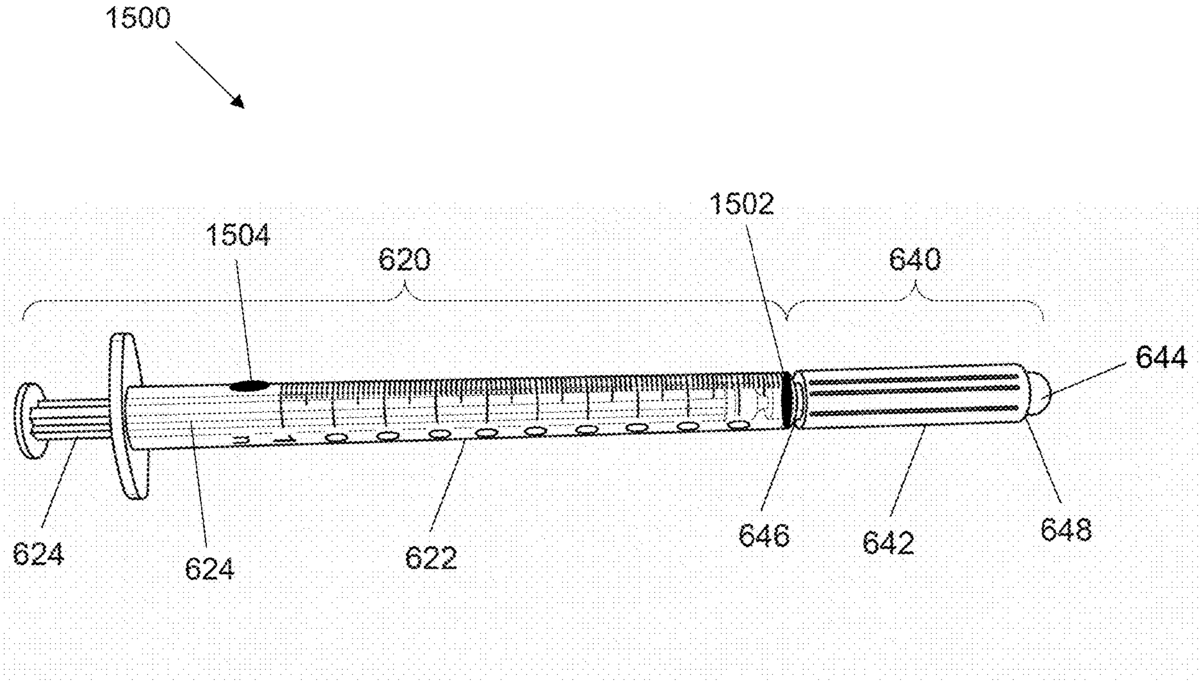
FIG. 15 shows an automated device for applying and/or delivering topical compounds, the device having an area that can be physically manipulated to automatically filter the topical compounds, according to at least one embodiment of the present disclosure.

Turning now to FIG. 15, an automated device 1500 for applying and/or delivering topical compounds is shown. The device 1500 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 1500 further comprises a filter 1502 that can be disposed inside the barrel or chamber 622 such that the topical compounds are filtered through the filter before delivery and/or administration (e.g., before movement through the tip portion 640). In at least one example, the filter is a 5 micron filter. Filtration using the filter 1502 can be automatic as the barrel or chamber 622 is being filled with one or more topical solutions. Alternatively or additionally, filtration using the filter 1502 occurs when an area 1504 is physically manipulated (e.g., moved, pressed, depressed, etc.) by a user. The area 1504 can be of any physically manipulatable construction (e.g., a tab, a lever, a button, etc.) and can be disposed anywhere on the device 1500. It should be appreciated that the filter 1502 and/or area 1504 may be used with any automated device described herein, and is not limited to the specific embodiment shown. Further, the filter 1502 and/or area 1504 may be used in combination with any one or more embodiments described below herein.

Figure 16:
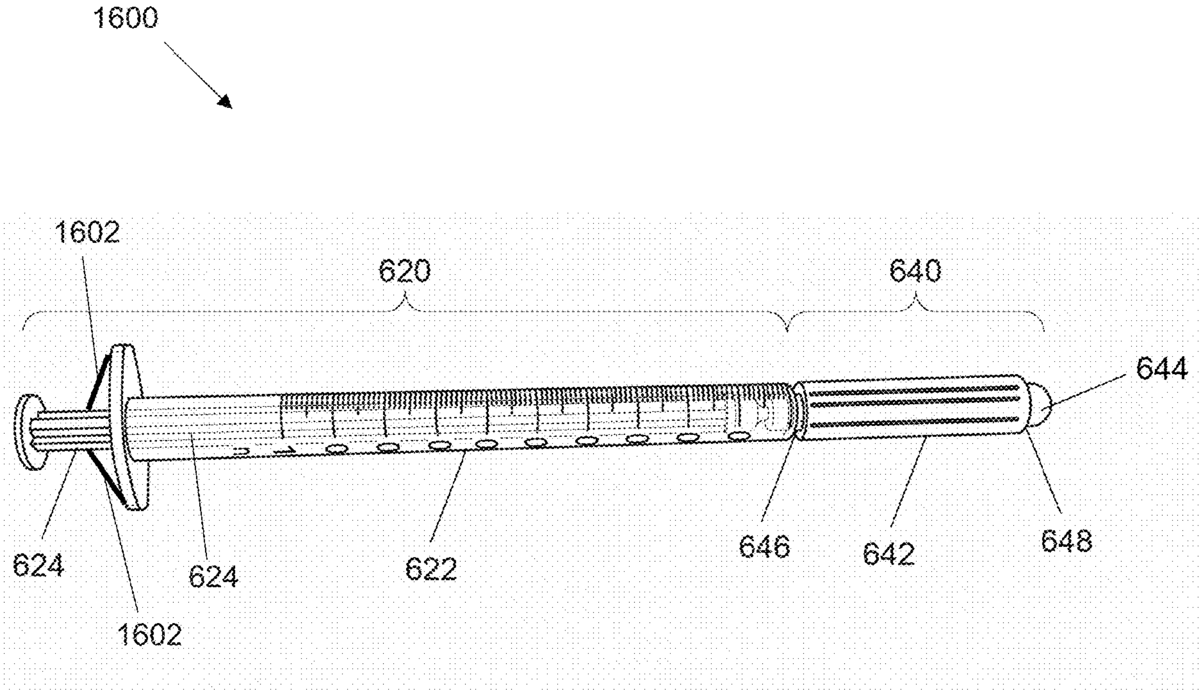
FIG. 16 shows an automated device for applying and/or delivering topical compounds, the device having automated locking mechanisms, according to at least one embodiment of the present disclosure.

Turning now to FIG. 16, an automated device 1600 for applying and/or delivering topical compounds is shown. The device 1600 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 1600 further comprises one or more locking mechanisms 1602 that lock and/or otherwise disable the plunger 624 once it has been fully depressed and/or all of the topical compounds in the device have been delivered, administered, and/or ejected through the tip portion 640. In at least one example, the one or more locking mechanisms 1602 activate automatically once the plunger 624 has been fully depressed and/or all of the topical compounds in the device have been delivered, administered, and/or ejected through the tip portion 640. It should be appreciated that the one or more locking mechanisms 1602 may be used with any automated device described herein, and is not limited to the specific embodiment shown. Further, the automated locking mechanism(s) 1602 may be used in combination with any one or more embodiments described below herein.

Figure 17:
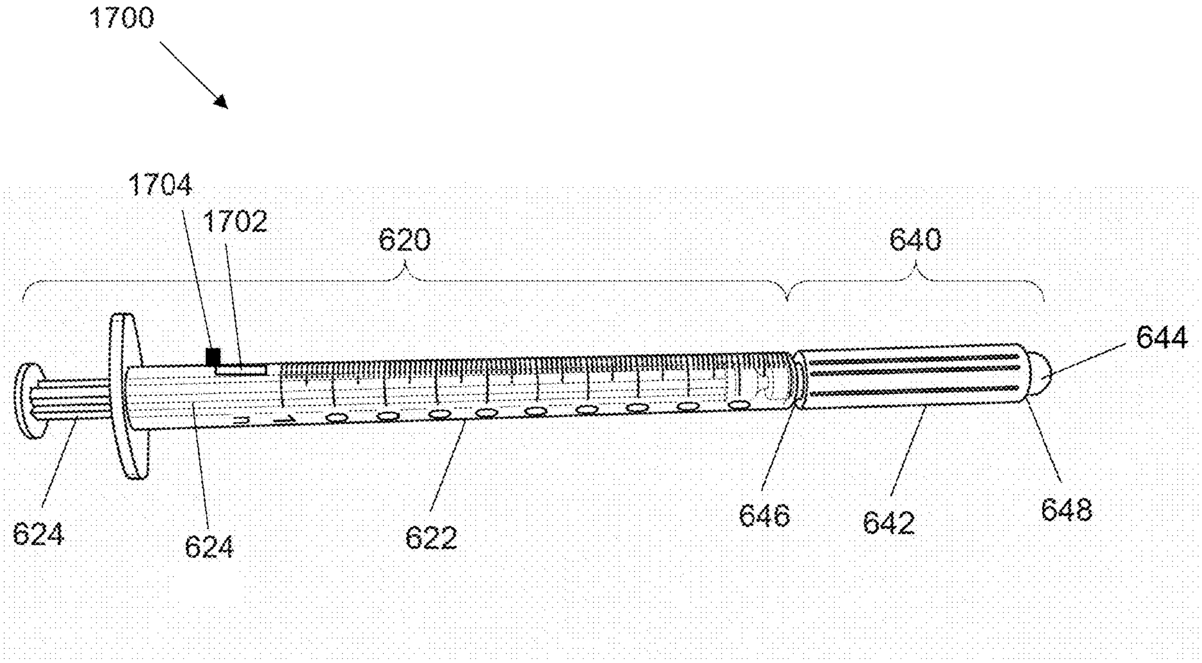
FIG. 17 shows an automated device for applying and/or delivering topical compounds, the device having an area that can be physically manipulated to automatically release additional agents from a storage area, according to at least one embodiment of the present disclosure.

Turning now to FIG. 17, an automated device 1700 for applying and/or delivering topical compounds is shown. The device 1700 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 1700 further comprises a storage area 1702 disposed inside the barrel or chamber 622 that can be automatically activated to release one or more additional agents into the barrel or chamber. Such agents may be any agents described herein, including, without limitation, lubricating agents, other agents that can be combined and/or co-administered with the one or more topical compounds, nanoparticles, peptides, and the like. Such agents may be released into the barrel either before, during, and/or after the topical compounds have been inserted into the barrel or chamber, and/or administered to a surface of human tissue (e.g., skin). The automatic activation of removal of agents from the storage area 1702 may be achieved when an area 1704 is physically manipulated (e.g., moved, pressed, depressed, etc.) by a user. The area 1704 can be of any physically manipulatable construction (e.g., a tab, a lever, a button, etc.) and can be disposed anywhere on the device 1700. It should be appreciated that the storage area 1702 and/or area 1704 may be used with any automated device described herein, and is not limited to the specific embodiment shown. Further, the storage area 1702 and/or area 1704 may be used in combination with any one or more embodiments described below herein.

Figure 18:
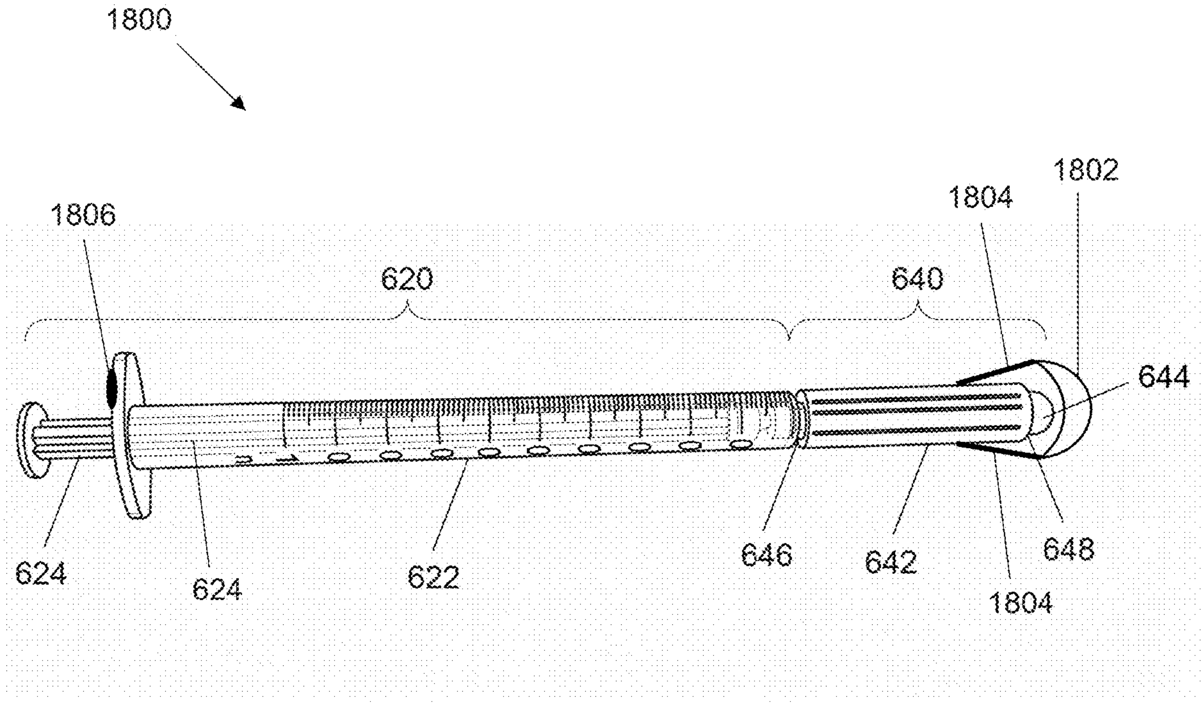
FIG. 18 shows an automated device for applying and/or delivering topical compounds, the device having an area that can be physically manipulated to automatically cover a portion of the device, according to at least one embodiment of the present disclosure.

Turning now to FIG. 18, an automated device 1800 for applying and/or delivering topical compounds is shown. The device 1800 comprises a syringe 620 and a tip portion 640 physically connected and/or attached to the syringe via a connector 646. The syringe 620 comprises a barrel or chamber 622. The connector 646 may be similar to, or the same as, any of the open connector ends described herein (e.g., connector end 206). The tip portion 640 comprises a body 642 disposed between the connector 646 and a delivery end 648. The tip portion 640 further comprises a membrane 644 physically attached and/or connected to the delivery end 648. The device 1800 further comprises a cover 1802 that can be moved and/or locked in place, via arms 1804, to cover the tip portion 640 or one or more portions thereof (e.g., membrane 644). Such a cover 1802 may be disposed to protect the tip portion 640 or one or more portions thereof (e.g., membrane 644) after the device 1800 has been used, and/or when the device is not in use. Accordingly, in at least one example, the cover 1802 helps ensure cleanliness of the device and prevention of contamination and/or leakage of any topical compounds contained within the device. Movement and/or locking of the cover 1802 and/or the arms 1804 can be achieved when an area 1806 is physically manipulated (e.g., moved, pressed, depressed, etc.) by a user. The area 1806 can be of any physically manipulatable construction (e.g., a tab, a lever, a button, etc.) and can be disposed anywhere on the device 1800. It should be appreciated that the cover 1802, the arms 1804, and/or the area 1806 may be used with any automated device described herein, and is not limited to the specific embodiment shown. Further, the cover 1802, the arms 1804, and/or the area 1806 may be used in combination with any one or more embodiments described below herein.

EXAMPLES

Example 1: Treatment of Burns

This example describes the administration of one or more compounds and/or medications to treat one or more burn injuries.

The devices and/or applicators described herein can be used to treat one or more burn injuries on a subject. After obtaining the device and/or applicator, the barrel of the syringe can be filled with an appropriate amount and/or concentration of one or more compounds and/or medications to treat burns. Such compounds and/or medications include antibacterial agents (e.g., polysporin, which is a combination of bacitracin zinc and polymyxin B sulfate, mupirocin, neomycin, erythromycin, and the like), antiseptic agents, antifungal agents, agents containing silver (e.g., silver sulfadiazine, nanocrystalline silver, silver nitrate, and the like), agents containing bismuth, cerium nitrate, mafenide acetate, chlorhexidine (e.g., chlorhexidine gluconate), povidone-iodine (which may be in a liposomal preparation), Dakin's solution (0.025% sodium hypochlorite), gentamicin sulfate, nitrofurazone, penetration enhancing agents (e.g., glycerin, saline, sodium dodecyl sulfate, ethanol, hexane:ethanol, ethyl acetate:ethanol dimethyl sulfoxide, glycine, terpenes, and the like), one or more growth factors (e.g., PDGF, TGF-β), suitable grafts (e.g., autogenous, allografts, synthetic and/or semi-synthetic skin substitutes, and the like) and/or dressings, and combinations thereof.

After the syringe barrel has been filled, an individual (e.g., a medical professional) can apply the compound and/or medication to the burn injury site by holding the device and/or applicator between at least one finger of their hand and their thumb. The individual can then exert sufficient force on the syringe barrel to move the compound and/or medication through the syringe tip and out through a closed end of the attached membrane. Once a suitable amount of the compound and/or medication has been expelled from the syringe barrel in such a fashion, that amount can be applied to the burn injury site by positioning the device and/or applicator such that the suitable amount of the compound and/or medication contacts the burn injury site. Application of the compound and/or medication can then be repeated as necessary.

Further protection of the burn injury site, such as covering the site with a gauze or other dressing, may be done in combination with applying the compounds and/or medications described above.

Application of the compounds and/or medications described above may be performed in combination, and/or in sequence, with one or more additional therapies to treat burns and/or burn injury sites.

Example 2: Treatment of Scars

This example describes the administration of one or more compounds and/or medications to treat one or more scars.

The devices and/or applicators described herein can be used to treat one or more scars on a subject. Such scars may result from burns, lacerations, and/or surgical incisions (e.g., due to a Cesarean section). Accordingly, scars can be painful to the subject, cause redness and/or itching, be aesthetically unappealing, and/or limit the function of tissue in and around the scarred area.

After obtaining the device and/or applicator, the barrel of the syringe can be filled with an appropriate amount and/or concentration of one or more compounds and/or medications to treat scars and/or prevent scarring. Such compounds and/or medications include steroids and/or corticosteroids (e.g., methylprednisolone, fluocinolone acetonide, triamcinolone acetonide, and the like), silicone (e.g., silicone gel), onion extract (extractum cepae), agents that act to cross-link DNA and/or prevent DNA replication (e.g., mitomycin C), agents that act as immune response modifiers (e.g., imiquimod, which can stimulate interferon, causing an increased breakdown of collagen), agents that inhibit collagen synthesis (e.g., bleomycin, which can act to inhibit collagen synthesis by decreasing stimulation by TGF-β1), interferons (e.g., interferon alfa-2b), botulinum toxin A (BTA), suitable grafts (e.g., autogenous, allografts, synthetic and/or semi-synthetic skin substitutes, and the like) and/or dressings, and combinations thereof.

After the syringe barrel has been filled, an individual (e.g., a medical professional) can apply the compound and/or medication to the scar and/or scar area by holding the device and/or applicator between at least one finger of their hand and their thumb. The individual can then exert sufficient force on the syringe barrel to move the compound and/or medication through the syringe tip and out through a closed end of the attached membrane. Once a suitable amount of the compound and/or medication has been expelled from the syringe barrel in such a fashion, that amount can be applied to the scar and/or scar area by positioning the device and/or applicator such that the suitable amount of the compound and/or medication contacts the scar and/or scar area. Application of the compound and/or medication can then be repeated as necessary.

Application of the compounds and/or medications described above may be performed in combination, and/or in sequence, with one or more additional scar therapies, such as cryotherapy, radiotherapy (e.g., brachytherapy, X-rays, and electron beams), laser therapy (e.g., via ablative and/or non-ablative lasers), mechanical pressure therapy, microneedling procedures, dermabrasion procedures, skin peels (e.g., chemical peels), collagen replacement therapies (e.g., collagen replacement injections), surgical scar revision treatments, adhesive microporous hypoallergenic paper tape, dynamic stress-shielding devices, and combinations thereof.

Follow-up management and/or assessment of the scar and/or scarred area may be performed by using, for instance, the modified Vancouver Scar Scale (MVSS), which assesses (A) scar pigmentation on a rating scale from "0" to "2" (where a "0" rating equates to a normal pigmentation, a "1" rating equates to hypo-pigmentation, and a "2" rating equates to hyperpigmentation), (B) vascularity on a rating scale from "0" to "5" (where a "0" rating equates to a normal color, a "1" rating equates to a pink color, a "2" rating equates to a pink to red color, a "3" rating equates to a red color, a "4" rating equates to a red to purple color, and a "5" rating equates to a purple color), (C) pliability on a rating scale from "0" to "5" (where a "0" rating equates to a normal pliability, a "1" rating equates to supple, a "2" rating equates to yielding, a "3" rating equates to firm, a "4" rating equates to banding-rope tissue, and a "5" rating equates to contracture), and (D) height on a rating scale from "0" to "3" (where a "0" rating equates to normal and/or flat, a "1" rating equates to a height of less than 2 millimeters, a "2" rating equates to a height of between 2-5 millimeters, and a "3" rating equates to a height of greater than 5 millimeters). Scar thicknesses can also be measured using, for example, linear probe ultrasounds.

Example 3: Treatment to Improve Skin Texture, Quality, and/or Clarity

This example describes the administration of one or more compounds and/or medications to improve skin texture, quality, and/or clarity (e.g., via one or more anti-aging compounds).

After obtaining the device and/or applicator, the barrel of the syringe can be filled with an appropriate amount and/or concentration of one or more compounds and/or medications to improve skin texture, quality, and/or clarity, to treat aging skin, and/or to prevent aging of skin. Such compounds and/or medications include phenols (e.g., resveratrol), nicotinamide nucleotides (e.g., nicotinamide mononucleotides, nicotinamide adenine dinucleotides, nicotinamide ribosides), curcumin, sirolimus (which may also be called rapamycin), coenzymes (e.g., coenzyme Q10), polyamines (e.g., spermidine), catechins (e.g., epigallocatechin gallate, which may also be called epigallocatechin-3-gallate), flavonoids (e.g., quercetin, flavonols such as fisetin), stilbenoids (e.g., pterostilbene), carotenoids (e.g., crocin, astaxanthin), carnosine, anthocyanins (which may also be called anthocyans), lignans (e.g., sesamin), tyrosol, piceatannol, hesperidin, ginsenosides (e.g., ginsenoside Rg1), geroprotectants, seaweed derivatives, nanoemulsions (which may be, for instance, biphasic colloidal dispersions containing multiple immiscible liquids and one or more emulsifiers), dendrimers, polymeric nanoparticles, carbon nanotubes, phytobioactive compounds, phytoantioxidants, nano-phytoantioxidants, lycopene, antibodies (e.g., monoclonal antibodies), enzymes (e.g., catalase, superoxide dismutase, peroxidases such as glutathione peroxidase), glutathione, lipoic acid (which may also be called α-lipoic acid or thioctic acid), pimagedine (which may also be called aminoguanidine), benzo-coumarins (which may also be called dibenzo-α-pyrones) (e.g., urolithin A), trimethylglycine, hormones (e.g., growth hormone (which may also be called somatotropin or human growth hormone in its human form)), proteins (e.g., chaperone proteins such as Hsp90), steroids (e.g., pregnenolone), vitamin A (which may also be called retinol) and vitamin A forms and/or derivatives, vitamin B and vitamin B forms and/or derivatives (e.g., niacinamide or nicotinamide), vitamin C and vitamin C forms and/or derivatives, vitamin D and vitamin D forms and/or derivatives, vitamin E and vitamin E forms and/or derivatives, and combinations thereof.

After the syringe barrel has been filled, an individual (e.g., a medical professional) can apply the compound and/or medication to one or more areas of skin by holding the device and/or applicator between at least one finger of their hand and their thumb. The individual can then exert sufficient force on the syringe barrel to move the compound and/or medication through the syringe tip and out through a closed end of the attached membrane. Once a suitable amount of the compound and/or medication has been expelled from the syringe barrel in such a fashion, that amount can be applied to the one or more skin areas by positioning the device and/or applicator such that the suitable amount of the compound and/or medication contacts the one or more skin areas. Application of the compound and/or medication can then be repeated as necessary.

Application of the compounds and/or medications described above may be performed in combination, and/or in sequence, with one or more additional therapies to improve skin texture, quality, and/or clarity, to treat aging skin, and/or to prevent aging of skin.

Example 4: Treatment Using Anti-Inflammatory Compounds

This example describes the administration of one or more compounds and/or medications to treat and/or prevent inflammation in one or more mammalian tissues (e.g., skin tissue, nerve tissue, muscle tissue, tendons, cartilage, ligaments, and the like). Accordingly, one or more of such compounds and/or medications can reduce inflammation (e.g., redness, swelling, and/or pain) in mammalian tissues. One or more of such compounds and/or medications may also block one or more substances in a mammalian subject that cause inflammation.

After obtaining the device and/or applicator, the barrel of the syringe can be filled with an appropriate amount and/or concentration of one or more compounds and/or medications to treat and/or prevent inflammation in one or more mammalian tissues and/or tissue types. Such compounds and/or medications include curcumin, colchicine, resveratrol, catechins (e.g., epigallocatechin gallate), flavonoids (e.g., quercetin, flavonols such as fisetin), anthocyanins, fatty acids (e.g., omega-3 fatty acid), phenolic compounds (e.g., oleocanthal), betaines, batalaines, capsaicin, limonin, ginsenosides (e.g., ginsenoside Rg1), luteolin, kaempferol, icariin, immune selective anti-inflammatory derivatives, selective glucocorticoid receptor agonists, resolvins, protectins, protein inhibitors (e.g., TNF inhibitors), polysaccharides (e.g., astragalus polysaccharide), minerals (e.g., selenium), enzymes (e.g., bromelain), vitamin E and vitamin E forms and/or derivatives, and combinations thereof.

After the syringe barrel has been filled, an individual (e.g., a medical professional) can apply the compound and/or medication to one or more areas of tissue that require prevention and/or treatment of inflammation by holding the device and/or applicator between at least one finger of their hand and their thumb. The individual can then exert sufficient force on the syringe barrel to move the compound and/or medication through the syringe tip and out through a closed end of the attached membrane. Once a suitable amount of the compound and/or medication has been expelled from the syringe barrel in such a fashion, that amount can be applied to the one or more areas of tissue by positioning the device and/or applicator such that the suitable amount of the compound and/or medication contacts the one or more areas of tissue. Thus, administration of the compound and/or medication can be performed on different types of tissues, such as skin tissue, neural tissue, muscle tissue, tendons, cartilage, ligaments, tissues of one or more organs, and the like. Application of the compound and/or medication can then be repeated as necessary.

Application of the compounds and/or medications described above may be performed in combination, and/or in sequence, with one or more additional therapies to treat and/or prevent inflammation.

Example 5: Treatments Using Adhesives, Sealants, and/or Hemostatic Agents

This example describes the administration of one or more compounds and/or medications that act as adhesives, sealants, and/or hemostatic agents. Such compounds and/or medications may be used in surgeries (e.g., cartilage repair surgery, liver surgery), in wound repair treatments (e.g., to treat injuries to the spleen, eyes, and other organs), to create clots for hemostasis, and to reduce pain and/or swelling in graft procedures (e.g., skin grafts). The aforementioned compounds and/or medications can further be used in conjunction with one or more grafts, implants, and the like, including, for instance, the outside of micro-vascular anastomosis, the outside of grafts (e.g., vein grafts, bone grafts, allografts, and/or other grafts), the outside of tendons, acellular dermal matrices, the outside of reconstructions (e.g., bone reconstructions), the outside of one or more artificial and/or synthetic implants (e.g., bone substitutes, peel substitutes, and the like), the outside of one or more bioengineered interfaces and/or bioengineered devices, the outside of bioengineered interfaces and/or bioengineered devices, and combinations thereof.

After obtaining the device and/or applicator, the barrel of the syringe can be filled with an appropriate amount and/or concentration of one or more compounds and/or medications that act as adhesives, sealants, and/or hemostatic agents. Such compounds and/or medications include fibrin sealants and/or fibrin-based glues, polyurethane-based adhesives (e.g., MAR-1), polyethylene glycol polymers, albumin (e.g., bovine serum albumin), glutaraldehyde, cyanoacrylates (e.g., octyl cyanoacrylate, butyl cyanoacrylate), gelatin-based hemostatic agents, collagen (e.g., bovine collagen), cellulose (e.g., oxidized regenerated cellulose), polysaccharide spheres, plasma liquids and/or derivatives, other sealants, adhesives, and/or hemostats, and combinations thereof.

After the syringe barrel has been filled, an individual (e.g., a medical professional) can apply the compound and/or medication to one or more areas of tissue that require adhesion, sealing, and/or hemostasis by holding the device and/or applicator between at least one finger of their hand and their thumb. The individual can then exert sufficient force on the syringe barrel to move the compound and/or medication through the syringe tip and out through a closed end of the attached membrane. Once a suitable amount of the compound and/or medication has been expelled from the syringe barrel in such a fashion, that amount can be applied to the one or more areas of tissue by positioning the device and/or applicator such that the suitable amount of the compound and/or medication contacts the one or more areas of tissue. Thus, administration of the compound and/or medication can be performed on different types of tissues, such as skin tissue, neural tissue, muscle tissue, tendons, cartilage, ligaments, tissues of one or more organs, and the like. Application of the compound and/or medication can then be repeated as necessary.

Application of the compounds and/or medications described above may be performed in combination, and/or in sequence, with one or more additional therapies for promoting wound healing, treating injuries, sealing injury and/or wound sites, and/or promoting hemostasis.

Example 6: Treatment Using Adipose-Derived Compounds and/or Tissue

This example describes the administration of one or more adipose-derived compounds and/or tissue, including nanofat, microfat, ASCs, and the like. Nanofat formulations have been described and include the following as a non-limiting example.

Briefly, nanofat formulations may be generated by first harvesting adipose tissue from a subject. For such harvesting, modified Klein solution (e.g., lidocaine 800 mg/L and adrenaline 1:1000000) is introduced into the abdomen. Adipose tissue is then harvested with a multiport 3 millimeter cannula with side holes of 1 millimeter in diameter. After harvesting, the adipose tissue is rinsed with saline, followed by filtration through a sterile cloth (e.g., a nylon cloth with 0.5 millimeter pore size) placed over a sterile container. Mechanical emulsification of the tissue is then performed by passing the tissue between two syringes connected by one or more connectors (e.g., luer-style connectors) for a minimum of 10, 20, or 30 passages. After such passages, the adipose tissue is converted into an emulsion. The emulsified tissue is then filtered over the sterile cloth again and the effluent, which is the nanofat, is collected in a sterile container.

After obtaining the device and/or applicator, the barrel of the syringe can be filled with an appropriate amount and/or concentration of one or more adipose tissue-derived compounds and/or tissue. Such compounds include nanofat, microfat, ASCs, and combinations thereof. Adipose-derived compounds and/or tissue, including nanofat, may be generally devoid of adipocytes, but contain a variety of ASCs, biological fragments (e.g., of arterioles, venules, and capillaries), growth factors (e.g., VEGF, PDGF, HGF, TGF-β, basic fibroblast growth factor (bFGF), insulin-like growth factor 1 (IGF-1), granulocyte-macrophage colony-stimulating factor (GM-CSF), and others), peptides (e.g., lipoxins, resolvins, protectins, neurotrophic factors, angiogenin, matrix metalloproteinases ("MMP" or "MMPs") such as MMP-9, leukemia inhibitory factor, macrophage migration inhibitory factor, and the like), and/or cytokines (e.g., IL-1RA, IL-4, IL-8, IL-10, IL-11, IL-13, and the like). Such adipose-derived compounds may be liquefied and applied to one or more mammalian tissue types due to their autologous nature. In some embodiments, the size of the individual components within the adipose-derived compounds (e.g., nanofat) is between 400 to 600 μm.

After the syringe barrel has been filled, an individual (e.g., a medical professional) can apply the compound and/or tissue to one or more areas of a subject that require grafting (e.g., areas of the face, areas of the hands, the decolletage, areas of the breasts, areas of the buttocks, areas of the genitals, and the like) by holding the device and/or applicator between at least one finger of their hand and their thumb. The individual can then exert sufficient force on the syringe barrel to move the compound and/or medication through the syringe tip and out through a closed end of the attached membrane. Once a suitable amount of the compound and/or medication has been expelled from the syringe barrel in such a fashion, that amount can be applied to the one or more areas of tissue by positioning the device and/or applicator such that the suitable amount of the compound and/or medication contacts the one or more areas. Thus, administration of the compound and/or medication can be performed to different types of tissues, such as skin tissue, breast tissue, and the like. Application of the compound and/or medication can then be repeated as necessary.

Application of the compounds and/or medications described above may be performed in combination, and/or in sequence, with one or more regenerative therapies for various treatments (e.g., plastic surgery treatments including facial rejuvenation, treatments that reduce skin wrinkles, facial volume augmentation treatments, and the like).

Example 7: Treatment Using Platelet-Rich Plasma (PRP)

This example describes the administration of one or more formulations containing platelet-rich plasma (PRP), which may also be referred to as "autologous conditioned plasma." Such formulations may be used in orthopedics (e.g., for muscle strains, tendon conditions, muscle-fascial injuries, arthritis, and the like), dermatology (e.g., for skin rejuvenation, wound healing, alopecia, and the like), oral surgery, plastic surgery, and combinations thereof.

Generally, PRP contains concentrated platelet-rich plasma protein that is derived from whole blood. Different types of PRP exist, including (1) pure PRP (P-PRP) (which may also be referred to as leucocyte-poor PRP), which generally has no or minimal leucocytes and a low-density fibrin network, (2) leucocyte-PRP (L-PRP), which generally contains leucocytes and a low-density fibrin network, (3) pure platelet-rich fibrin (P-PRF) (which may also be referred to as leucocyte-poor PRF), which generally has no or minimal leucocytes and a high-density fibrin network, and (4) leucocyte-PRF (L-PRF), which generally contains leucocytes and a high-density fibrin network.

PRP formulations have been described and include the following two methods as non-limiting examples: (1) preparation by the PRP method, and (2) preparation by the buffy coat method.

Briefly, preparation by the PRP method begins by withdrawing and collecting whole blood. A first centrifugation is performed, after which the whole blood is separated into three layers: (1) an upper layer that contains mostly platelets and white blood cells, (2) an intermediate layer referred to as the "buffy coat," which contains white blood cells, and (3) a bottom layer that contains mostly red blood cells. For the production of P-PRP, the upper layer and the intermediate buffy coat layer are then transferred to another tube. For the production of L-PRP, the buffy coat layer and a portion of the red blood cells are transferred to another tube. A second centrifugation is then performed to concentrate platelets. An upper portion, which generally contains platelet-poor plasma, is then removed. The pellet is then homogenized in plasma to create PRP.

Preparation by the buffy coat method begins by withdrawing and collecting whole blood. A first centrifugation is performed at relatively high speed, after which the whole blood is separated into three layers: (1) an upper layer that contains mostly platelet-poor plasma, (2) an intermediate layer referred to as the "buffy coat," which contains platelets and white blood cells, and (3) a bottom layer that contains mostly red blood cells. The buffy coat layer is removed and subjected to a second centrifugation to separate the white blood cells. Alternatively and/or additionally, a leucocyte filtration filter may be used to filter out the leucocytes.

After obtaining the device and/or applicator, the barrel of the syringe can be filled with an appropriate amount and/or concentration of one or more PRP formulations. Such formulations may include various growth factors and/or cytokines (e.g., PDGF, TGF-β, fibroblast growth factor (FGF), insulin-like growth factors, VEGF, epidermal growth factors, interleukins, keratinocyte growth factor, connective tissue growth factor, HGF, stromal cell-derived factors, endostatins, and the like).

After the syringe barrel has been filled, an individual (e.g., a medical professional) can apply the one or more PRP formulations to one or more tissues in a subject by holding the device and/or applicator between at least one finger of their hand and their thumb. The individual can then exert sufficient force on the syringe barrel to move the one or more PRP formulations through the syringe tip and out through a closed end of the attached membrane. Once a suitable amount of the one or more PRP formulations has been expelled from the syringe barrel in such a fashion, that amount can be applied to the one or more areas of tissue by positioning the device and/or applicator such that the suitable amount of the one or more PRP formulations contacts the one or more areas. Thus, administration of the one or more PRP formulations can be performed to different types of tissues, such as skin tissue, nerve tissue, muscle tissue, bone tissue, tendons, cartilage, ligaments, gum tissue, and the like. Application of the one or more PRP formulations can then be repeated as necessary.

Application of the one or more PRP formulations described above may be performed in combination, and/or in sequence, with one or more therapies and/or treatments (e.g., orthopedic treatments, dermatology treatments, oral surgery treatments, plastic surgery treatments, and the like).

Example 8: Treatment Using Exosomes

This example describes the administration of one or more formulations containing exosomes. Such formulations may be used to treat one or more diseases or disorders (e.g., cancers, tumors, and the like).

Exemplary methods for induction of exosomes from stem cells include treatment of the stem cells with cytokines, treatment with liposome stimulation using one or more stimulant liposomes such as neutral or cationic liposomes, and/or other physical and/or biological methods previously described and referenced herein. One or more such methods may be optimized to maximize the number of exosomes present in the one or more formulations, for example, 90%, 80%, 70%, 60%, 50%, 40%, or more than 30%. Generally, methods of isolating exosomes may include one or more of differential ultracentrifugation-based techniques, size-based techniques, immunoaffinity capture-based techniques, exosome precipitation, and microfluidics-based techniques. See, e.g., Li P et al., *Theranostics,* 7 (3): 789-804 (2017). In some embodiments, the one or more formulations include isolated exosomes and/or exogenous exosomes generated ex vivo from amniotic fluid mesenchymal stem cells ("MSC" or "MSCs") and/or derived from MSCs of another source. In at least another embodiment, the one or more formulations include a number of engineered exosomes in a range of about $1\times10^{2}$ to about $1\times10^{20}$; for example, in a range of about $1\times10^{2}$ to about $1\times10^{16}$, about $1\times10^{2}$ to about $1\times10^{12}$, about $1\times10^{2}$ to about $1\times10^{10}$, about $1\times10^{2}$ to about $1\times10^{6}$, about $1\times10^{6}$ to about $1\times10^{20}$, about $1\times10^{6}$ to about $1\times10^{12}$, about $1\times10^{6}$ to about $1\times10^{10}$, about $1\times10^{10}$ to about $1\times10^{20}$, about $1\times10^{12}$ to about $1\times10^{20}$, or about $1\times10^{16}$ to about $1\times10^{20}$.

After obtaining the device and/or applicator, the barrel of the syringe can be filled with an appropriate amount and/or concentration of one or more formulations containing exosomes. Such formulations may include one or more miRNAs (e.g., let 7a, miRNA 218, miRNA 9-5p, miRNA 19a-3p, miRNA 30a-5p, miRNA 212-5p, miRNA 323-5p, miRNA 15a, miRNA 15b, miRNA 16, miRNA 424, miRNA 497, and the like), osteoinductive factors (e.g., transforming growth factors (TGFs), bone morphogenetic proteins (BMPs), fibroblast growth factors (FGFs), insulin-like growth factors (IGFs), platelet-derived growth factors (PDGFs), osterix (OSX), one or more members of the Runx family of transcription factors, and the like), neuronal regeneration factors (e.g., c-Jun, activating transcription factor-3 (ATF-3), SRY-box containing gene 11 (Sox11), small proline-repeat protein 1A (SPRRIA), growth-associated protein-43 (GAP-43), CAP-23, and the like), immunomodulatory factors (e.g., cytokines, interferon, interleukin, antigens, growth factors, any agent that upregulates at least one member of the LXR-alpha, STAT6, and P13/Akt pathways, and the like), extracellular matrix binding factors (e.g., integrin α5, any agent that increases the binding affinity or rate to one or more components of the extracellular matrix and/or extracellular matrix-derivative peptides in a dose-dependent manner), and the like. In some embodiments, the components of the extracellular matrix include one or more of proteins (e.g., collagen, elastin, fibrin, and the like), glycoproteins (e.g., fibronectins, laminins, and the like), proteoglycans, polysaccharides (e.g., hyaluronic acid, alginate, heparin functionalized with extracellular matrix proteins or extracellular matrix-derivative peptide motifs, polylactic acid (PLA) functionalized with extracellular matrix proteins or extracellular matrix-derivative peptide motifs, polyglycolic acid (PGA) functionalized with extracellular matrix proteins or extracellular matrix-derivative peptide motifs, and the like), collagen type I (COL1) protein, and/or fibronectin 1 (FN1) protein.

The one or more formulations may also include one or more carriers, including polymer carriers (e.g., a biodegradable polymer carrier), biocompatible polymers, and/or oligomers. Non-limiting examples of biocompatible polymers or oligomers include, but are not limited to, alginate, agarose, hyaluronic acid/hyaluronan, polyethylene glycol, poly(lactic acid), poly(vinyl alcohol), polyanhydrides, poly(glycolic acid), collagen, gelatin, heparin, glycosaminoglycans, saccharides (e.g., glucose, galactose, fructose, lactose, and sucrose), self-assembling peptides, and the like. The carriers may be present in an amount of 1% to 20% by weight based on the total weight of the formulation. For instance, the carrier can be present in the amount of 1 wt % to 15 wt %, 1 wt % to 10 wt %, 1 wt % to 5 wt %, 5 wt % to 20 wt %, 5 wt % to 15 wt %, 5 wt % to 10 wt %, 10 wt % to 20 wt %, 10 wt % to 15 wt %, or 15 wt % to 20 wt %, based on the total weight of the formulation.

After the syringe barrel has been filled, an individual (e.g., a medical professional) can apply the one or more formulations containing exosomes to one or more tissues in a subject by holding the device and/or applicator between at least one finger of their hand and their thumb. The individual can then exert sufficient force on the syringe barrel to move the one or more formulations through the syringe tip and out through a closed end of the attached membrane. Once a suitable amount of the one or more formulations has been expelled from the syringe barrel in such a fashion, that amount can be applied to the one or more areas of tissue by positioning the device and/or applicator such that the suitable amount of the one or more formulations contacts the one or more areas. Thus, administration of the one or more formulations can be performed to different types of tissues, such as skin tissue, nerve tissue, muscle tissue, bone tissue, tendons, cartilage, ligaments, gum tissue, and the like. Application of the one or more formulations containing exosomes can then be repeated as necessary.

Application of the one or more formulations described above may be performed in combination, and/or in sequence, with one or more other therapies and/or treatments (e.g., cancer treatments, bone reconstruction treatments, bone regeneration treatments, skin treatments, and the like).

In summary, embodiments of the disclosure described herein enable the application and/or delivery of one or more topical compounds in a controlled and precise way, preventing over-application of the compounds and ensuring application to the desired area. Embodiments of the disclosure are configured to connect to one or more types of known syringes via one or more types of known syringe tips. Users may hold the syringe as a pen or pencil, exerting force on an outside surface of the syringe barrel to apply the one or more topical compounds.

These and other objectives and features of the invention are apparent in the disclosure, which includes the above and ongoing written specification.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

I claim:

1. An automated device for delivering one or more topical compounds to a surface of mammalian tissue, the device comprising:

one or more automated portions;

one or more areas, on an outer surface of the device, configured to be physically manipulated by a user;

a chamber configured to hold the one or more topical compounds, the chamber comprising a filter disposed inside the chamber; and a tip portion connected to the chamber, the tip portion comprising a cap and a membrane, the cap comprising an open connector end, an open delivery end disposed opposite the open connector end and fluidly connected to the open connector end, and a cap body disposed between and connecting the open connector end and the open delivery end, wherein the membrane is physically attached to the open delivery end and is selectively permeable such that the membrane permits the one or more topical compounds to move through the membrane, and wherein the selective permeability of the membrane is configured to differ based on a biological, chemical, or physical nature of the one or more topical compounds, wherein the physical manipulation of the one or more areas activates the one or more automated portions to automatically load at least a portion of the one or more topical compounds from the chamber into the tip portion without the at least a portion of the one or more topical compounds being released out of the membrane, wherein the one or more topical compounds are filtered through the filter before delivery or administration and before movement through the tip portion, and wherein filtration through the filter occurs when the one or more areas are physically manipulated by the user, and wherein the one or more topical compounds are configured to be physically moved out of the chamber, through the membrane, and out of one end of the device, to be delivered to the surface of mammalian tissue.

2. The device of claim 1, wherein the one or more areas are selected from the group consisting of: a tab, a lever, a button, and combinations thereof.

3. The device of claim 1, wherein the one or more automated portions comprise a plunger and/or ejector.

4. The device of claim 3, wherein the plunger and/or ejector operate under electric power.

5. The device of claim 1, wherein the one or more automated portions comprise a connection between the chamber and the tip portion that delivers the one or more topical compounds.

6. The device of claim 5, wherein attachment between the chamber and the tip portion is automated.

7. The device of claim 5, wherein detachment between the chamber and the tip portion is automated.

8. The device of claim 1, further comprising one or more capsules containing the one or more topical compounds, and wherein removal of the one or more topical compounds from the one or more capsules is automated.

9. The device of claim 8, wherein the removal is triggered by the physical manipulation of the one or more areas.

10. The device of claim 1, wherein the one or more topical compounds are configured to be automatically moved from the chamber into the tip portion connected to the chamber.

11. The device of claim 10, wherein the automatic movement is triggered by the physical manipulation of the one or more areas.

12. The device of claim 1, wherein the automatic loading of at least the portion of the one or more topical compounds from the chamber into the tip portion comprises automatically aspirating a liquid and/or solution into the chamber.

13. The device of claim 1, wherein a plunger and/or ejector is configured to automatically eject air in the chamber before loading of the one or more topical compounds into the chamber.

14. The device of claim 13, wherein the automatic ejection is triggered by the physical manipulation of the one or more areas.

15. The device of claim 1, further comprising one or more automated sensors configured to detect a proximity of the device to the surface of mammalian tissue.

16. The device of claim 1, further comprising one or more locking mechanisms that are triggered by the physical manipulation of the one or more areas.

17. The device of claim 1, further comprising a storage area within the chamber, wherein release of one or more agents from the storage area is triggered by the physical manipulation of the one or more areas.

18. The device of claim 1, further comprising a cover that is automatically moveable to cover an area of the device for delivering the one or more topical compounds, wherein the automatic movement is triggered by the physical manipulation of the one or more areas.

19. The device of claim 1, wherein the membrane comprises an open inner end, a neck portion, and an outer end, wherein the open inner end and the neck portion are inserted into the open delivery end such that the outer end is disposed outside of the open delivery end.

20. The device of claim 19, wherein the physical manipulation of the one or more areas triggers automatic aspiration of liquid into the device by being aspirated through the membrane into the tip portion or the chamber.

21. The device of claim 1, further comprising one or more automated sensors configured to detect whether the membrane is touching the surface of mammalian tissue or is at a pre-determined distance from the surface of mammalian tissue, and wherein the one or more automated sensors are configured to activate an automated alarm or other notification to notify a user to prevent improper use or misuse of the device.

22. The device of claim 1, further comprising a cover configured to move or lock in place to cover the tip portion or the membrane, wherein the cover is movable via one or more arms, and wherein movement or locking of the cover or the one or more arms is triggered by the physical manipulation of the one or more areas.

* * * * *